US008815837B2

(12) United States Patent
Finch et al.

(10) Patent No.: US 8,815,837 B2
(45) Date of Patent: Aug. 26, 2014

(54) RESPIRATORY DISEASE TREATMENT

(75) Inventors: Harry Finch, Buckinghamshire (GB);
Craig Fox, Buckinghamshire (GB);
Mohammed Sajad, Essex (GB);
Monique Bondil Van Niel, Essex (GB);
Andrew Forrest, Essex (GB)

(73) Assignee: Pulmagen Therapeutics (Inflammation) Limited, Buckinghamshire (GB)

( * ) Notice: Subject to any disclaimer, the term of this patent is extended or adjusted under 35 U.S.C. 154(b) by 0 days.

(21) Appl. No.: 13/537,503

(22) Filed: Jun. 29, 2012

(65) Prior Publication Data

US 2012/0264787 A1 Oct. 18, 2012

Related U.S. Application Data

(60) Division of application No. 12/850,318, filed on Aug. 4, 2010, now Pat. No. 8,236,786, which is a continuation-in-part of application No. PCT/GB2009/001920, filed on Aug. 5, 2009.

(30) Foreign Application Priority Data

| Aug. 7, 2008 | (GB) | 0814488.3 |
| Dec. 24, 2008 | (GB) | 0823568.1 |
| Aug. 5, 2009 | (GB) | 0913672.2 |

(51) Int. Cl.
*A01N 43/00* (2006.01)

(52) U.S. Cl.
USPC .......................................... 514/183; 514/342

(58) Field of Classification Search
None
See application file for complete search history.

(56) References Cited

U.S. PATENT DOCUMENTS

| 6,127,394 | A | 10/2000 | Pershadsingh et al. |
| 8,236,786 | B2 | 8/2012 | Finch et al. |
| 2002/0055651 | A1 | 5/2002 | Moran et al. |
| 2004/0229904 | A1 | 11/2004 | Bunnage et al. |
| 2004/0242622 | A1 | 12/2004 | Mammen et al. |
| 2005/0133417 | A1 | 6/2005 | Bhan et al. |
| 2005/0159448 | A1 | 7/2005 | McKinnell et al. |
| 2005/0171147 | A1 | 8/2005 | Brown et al. |
| 2005/0182091 | A1 | 8/2005 | Brown et al. |
| 2005/0209292 | A1 | 9/2005 | Chuang et al. |
| 2005/0272769 | A1 | 12/2005 | Linsell |
| 2006/0019991 | A1 | 1/2006 | McKinnell et al. |
| 2006/0106075 | A1 | 5/2006 | Cuenoud et al. |
| 2006/0106213 | A1 | 5/2006 | Konetzki et al. |
| 2006/0160867 | A1 | 7/2006 | Freedman |
| 2007/0053868 | A1* | 3/2007 | Chidambaram et al. ... 424/78.38 |
| 2008/0254053 | A1* | 10/2008 | Mullally .................... 424/193.1 |

FOREIGN PATENT DOCUMENTS

| DE | 1025869 | | 3/1958 |
| EP | 0505321 | A2 | 3/1992 |
| EP | 1440966 | A1 | 7/2004 |
| EP | 1460064 | A1 | 9/2004 |
| EP | 1477167 | A1 | 11/2004 |
| EP | 2221048 | A1 * | 8/2010 |
| GB | 2335597 | A | 9/1999 |
| JP | 5025045 | A | 2/1993 |
| JP | 2005513031 | | 5/2005 |
| JP | 2005200419 | | 7/2005 |
| WO | 93/18007 | A1 | 9/1993 |
| WO | 99/64035 | A1 | 12/1999 |
| WO | 00/32585 | A1 | 6/2000 |
| WO | 00/53601 | A1 | 9/2000 |
| WO | 00/62766 | A2 | 10/2000 |
| WO | 00/75114 | A1 | 12/2000 |
| WO | 01/42193 | A1 | 6/2001 |
| WO | 01/82873 | A2 | 11/2001 |
| WO | 01/82980 | A1 | 11/2001 |
| WO | 01/83462 | A1 | 11/2001 |
| WO | 02/10143 | A1 | 2/2002 |
| WO | 02/12265 | A1 | 2/2002 |
| WO | 02/12266 | A1 | 2/2002 |
| WO | 02/13812 | A1 | 2/2002 |
| WO | WO 02056871 | A2 * | 7/2002 |
| WO | 02/066422 | A1 | 8/2002 |
| WO | 02/070490 | A1 | 9/2002 |
| WO | 02/076933 | A1 | 10/2002 |
| WO | 02/100879 | A1 | 12/2002 |
| WO | 03/024439 | A1 | 3/2003 |
| WO | 03/042160 | A1 | 5/2003 |
| WO | 03/042164 | A1 | 5/2003 |
| WO | 03/042229 | A1 | 5/2003 |
| WO | 03/045383 | A1 | 6/2003 |
| WO | 03/048181 | A1 | 6/2003 |
| WO | WO 03045383 | A1 * | 6/2003 |

(Continued)

OTHER PUBLICATIONS

Ghanim et al, J Clin Endocrinol Metab. Sep. 2006;91(9):3553-8. Epub Jun. 27, 2006.*
Kim et al, Mol. Pharmacol. 68:1568-1575, 2005.*
Crim et al, clinical therapeutic vol. 23, No. 9, 2001.*
Norman, Expert Opin. Ther. Patents Sep (2008) 18(9):1091-1096.*
Jamali et al, J Pharm Biomed Anal. Jan. 7, 2008; 46(1):82-7. Epub Sep. 8, 2007.*
EMEA (2006).*
Cazzola et al, British Journal of Pharmacology, 155, 291-299; 2008. 284; published online Jul. 7, 2008.*
Akiba K. et al. (1974) Bull. Chem. Soc. Jpn., 47: 935-937.

(Continued)

*Primary Examiner* — Wu-Cheng Winston Shen
*Assistant Examiner* — Jean Cornet
(74) *Attorney, Agent, or Firm* — Morgan, Lewis & Bockius LLP

(57) ABSTRACT

There is provided a pharmaceutical composition that is adapted for pulmonary administration by inhalation, which composition comprises a glitazone, such as pioglitazone or rosiglitazone, and one or more pharmaceutically acceptable carriers and/or excipients, and wherein the glitazone content of the composition consists of at least 95% by weight of the 5R enantiomer and less than 5% by weight of the 5S enantiomer. There is also provided a use and kit.

17 Claims, 2 Drawing Sheets

(56) References Cited

FOREIGN PATENT DOCUMENTS

| | | |
|---|---|---|
| WO | 03/062259 A2 | 7/2003 |
| WO | 03/072539 A1 | 9/2003 |
| WO | 03/091204 A1 | 11/2003 |
| WO | 03/099764 A1 | 12/2003 |
| WO | 2004/016578 A2 | 2/2004 |
| WO | 2004/016601 A1 | 2/2004 |
| WO | 2004/022547 A1 | 3/2004 |
| WO | 2004/032921 A1 | 4/2004 |
| WO | 2004/033412 A1 | 4/2004 |
| WO | 2004/037768 A2 | 5/2004 |
| WO | 2004/037773 A1 | 5/2004 |
| WO | 2004/037807 A2 | 5/2004 |
| WO | 2004/039762 A1 | 5/2004 |
| WO | 2004/039766 A1 | 5/2004 |
| WO | 2004/045618 A2 | 6/2004 |
| WO | 2004/046083 A1 | 6/2004 |
| WO | 2004/071388 A2 | 8/2004 |
| WO | 2004/080964 A1 | 9/2004 |
| WO | 2004/087142 A1 | 10/2004 |
| WO | 2004/089892 A2 | 10/2004 |
| WO | 2004/108675 A1 | 12/2004 |
| WO | 2004/108676 A1 | 12/2004 |
| WO | 2005/003098 A1 | 1/2005 |
| WO | 2005/033121 A2 | 4/2005 |
| WO | 2005/034939 A1 | 4/2005 |
| WO | 2005/035502 A1 | 4/2005 |
| WO | 2005/035518 A1 | 4/2005 |
| WO | 2005/040103 A1 | 5/2005 |
| WO | 2005/044787 A1 | 5/2005 |
| WO | 2005/058299 A1 | 6/2005 |
| WO | 2005/058867 A1 | 6/2005 |
| WO | 2005/065650 A2 | 7/2005 |
| WO | 2005/066140 A1 | 7/2005 |
| WO | 2005/070908 A1 | 8/2005 |
| WO | 2005/077361 A1 | 8/2005 |
| WO | 2005/080313 A2 | 9/2005 |
| WO | 2005/080324 A1 | 9/2005 |
| WO | 2005/090288 A1 | 9/2005 |
| WO | 2005/092087 A2 | 10/2005 |
| WO | 2005/092840 A1 | 10/2005 |
| WO | 2005/092841 A1 | 10/2005 |
| WO | 2005/092860 A1 | 10/2005 |
| WO | 2005/092861 A1 | 10/2005 |
| WO | 2005/092870 A1 | 10/2005 |
| WO | 2005/092887 A1 | 10/2005 |
| WO | 2005/110359 A1 | 11/2005 |
| WO | 2005/110990 A1 | 11/2005 |
| WO | 2005/111002 A2 | 11/2005 |
| WO | 2005/111005 A1 | 11/2005 |
| WO | 2005/121065 A2 | 12/2005 |
| WO | 2006/014704 A1 | 2/2006 |
| WO | 2006/016245 A1 | 2/2006 |
| WO | 2006/031556 A2 | 3/2006 |
| WO | 2006/032627 A1 | 3/2006 |
| WO | 2006/051373 A1 | 5/2006 |
| WO | 2006/056471 A1 | 6/2006 |
| WO | 2006/117664 | 11/2006 |
| WO | 2008/010089 | 1/2008 |
| WO | 2008/096112 A1 | 8/2008 |
| WO | 2008/096119 A1 | 8/2008 |
| WO | 2008/104790 A1 | 9/2008 |

OTHER PUBLICATIONS

Bartsch R.A. et al. (2001) Experimental and theoretical studies on the thermal decomposition of heterocyclic nitrosimines, JACS, 123: 7479.

Birrell M.A. et al. (2004) PPAR-γ agonists as therapy for diseases involving airway neutrophilia, Eur. Respir. J.,vol. 24: p. 18-23.

Campbell I.W. (2005) Curr. Mol. Med, 5:349-63.

Cantello B.C.C. et al. (1994) Facile biocatalytic reduction of the carbon-carbon double bond of 5-benzylidenethiazolidine-2,4-diones. Synthesis of (±)-5-(4-{2-[methyl(2-pyridyl)aminio]ethoxy}benzyl)thiazolidine-2,4-dione (BRL 49653), its (R) -(+)-enantiomer and analogues, J. Chem. Soc. Perkin Trans. I, 3319-3324.

Clark D.A. et al. (1991) Substituted dihydrobenzopyran and dihydrobenzofuran thiaolidine-2,4-diones as hypoglycemic agents, J. Med. Chem., vol. 34, p. 319-25.

Crossno J.T. Jr. et al. (2007) Rosiglitazone attenuates hypoxia-induced pulmonary arterial remodeling, Am. J. Physiol. Lung Cell. Mol. Physiol., vol. 292, p. L885-897.

Curkendall S.M. et al. (2006) Cardiovascular Disease in Patients with Chronic Obstructive Pulmonary Disease, Saskatchewan Canada Cardiovascular Disease in COPD Patients, Ann. Epidemiol., vol. 16, p. 63-70.

Cuzzocrea S. et al. (2003) Reduction in the Evolution Murine Type III Collagen-Induced Arthritis by Treatment With Rosiglitazone, a Ligand of the Peroxisome Proliferator-Activated Receptor γ, Arthritis Rheumatism, vol. 48, p. 3544-3556.

Cuzzocrea S. et al. (2004) Rosiglitazone, a ligand of the peroxisome proliferator-actived receptor-γ, reduces acute inflammation, European Journal of Pharmacology, vol. 483, p. 79-93.

Desreumanux P. et al. (2001) Attenuation of Colon Inflammation through Activators of the Retinoid X Receptor (RXR)/Peroxisome Proliferator-activated Receptor γ (PPARγ) Heterodimer: a basis for new therapeutic strategies, J. Exp. Med. vol. 193, p. 827-838.

Eyles JE, et al. (1999) Immunological responses to nasal delivery of free and encapsulated tetanus toxoid: studies on the effect of vehicle volume, International Journal of Pharmaceutics, vol. 189, p. 75-9.

Faigl F. et. al. (2008) "Strategies in optical resolution: a practical guide", Tetrahedron: asymmetry, 19, 519-536.

Falck J.R. et al. (2008) Electrophilic α-Thiocyanation of Chiral and Achiral N-Acyl Imides. A Convenient Route to 5-substituted and 5,5-disubstituted 2,4-Thiazolidinediones, Bioorg. Med.Chem.Lett., vol. 18, p. 1768-1771.

Feinstein D.L. et al. (2002) Peroxisome Proliferator-Activated Receptor-γ Agonists Prevent Experimental Autoimmune Encephalomyelitis, Ann. Neurol., vol. 51, p. 694-702.

Guan Y.-F.et al. (2005) Thiazolidinediones expand body fluid volume through PPARγ stimulation of ENaC-mediated renal salt absorption, Nature Medicine, vol. 11, p. 861-866.

Haffner S.M. et al. (2002) Effect of Rosiglitazone Treatment on Nontraditional Markers of Cardiovascular Disease in Patients with Type 2 Diabetes Mellitus, Circulation, vol. 106, p. 679-684.

Hetzel M. et al. (2003) Inhibition of MMP-9 expression by PPARγ activators in human bronchial epithelial cells, Thorax, vol. 58, p. 778-783.

Izumi T. et al. (1997) Pharmacokinetic Stereoselectiveity of Troglitazone, an antidiabetic agent, in the KK Mouse, Biopharmaceutics and Drug Disposition, 18: 305-24.

Lausecker B. et al. (2006) Determination of the enantiomeric composition of a new insulin sensitizer in plasma samples from non-clinical and clinical investigations using chiral HPLC with electrospray tandem mass spectrometic detection, J. Chromatography, vol. 835, p. 40-46.

Lee K.S. et al. (2005) Ppar-gamma modulates allergic inflammation through up-regulation fo PTEN, FASEB Journal, vol. 19, p. 1033-1035.

Marx N. et al. (2003) Antidiabetic PPARγ-Activator Rosiglitazone Reduces MMP-9 Serum Levels in Type 2 Diabetic Patients with Coronary Artery Disease, Arterioscler. Thromb. Vasc. Biol. vol. 23, p. 283-288.

Milam J.E. et al. (2008) PPAR-γ agonists inhibit profibrotic phenotypes in human lung fibroblasts and bleomycin-induced pulmonary fibrosis, Am. J. Physiol. Lung Cell. Mol. Physiol., vol. 294, p. L891-901.

Padeletti M. et al. (2008) Coexistent chronic obstructive pulmonary disease and heart failure in the elderly, International Journal of Cardiology, vol. 125, p. 209-215.

Parks D.J. et al. (1998) Differential Activity of Rosiglitazone Enantiomers at PPARγ, Bioorganic & Medicinal Chemistry Letters, vol. 8, p. 3657-3658.

Reddy R.C. et al. (2004) Deactivation of murine alveolar macrophages by peroxisome proliferator-actived receptor-γ ligands, Am. J. Physiol. Lung Cell. Mol. Physiol., vol. 286, p. L613-619.

(56) References Cited

OTHER PUBLICATIONS

Rippley R.K. et al. (2007) Human Pharmacokinetics and Interconversion of Enantiomers of MK-0767, a Dual PPARα/γ Agonist, J.Clin. Pharmacol., vol. 47, 323-333.

Sanchez-Hidalgo M. et al. (2005) Rosiglitazone, an agonist of peroxisome proliferator-activated receptor gamma, reduces chronic colonic inflammation in rats, Biochemical Pharmacology, vol. 69, p. 1733-1744.

Shen Z. et al. (2005) Enantionmer ratio of MK-0767 in humans and nonclinical species, Rapid Communications in Mass Spectrometry, vol. 19, p. 1125-1129.

Shiojirit. et al. (2002) PPARγ ligands inhibit nitrotyrosine formation and inflammatory mediator expressions in adjuvant-induced rheumatoid arthritis mice, European Journal of Pharmacology, vol. 448, p. 231-238.

Sohda T. et al. (1984) Studies on antidiabetic agents. VI. Asymmetric Transformation of (±)-5-[4-(1-Methylcyclohexylmethoxy)benxyl]-2,4-thiazolidinedione(Ciglitazone) with Optically Active 1-Penylethylamines, Chem. Pharm. Bull., 32, 4460-65.

Ward J.E. et al. (2004) PPARγ ligands, 15-deoxy-Δ12,14-prostaglandin J2 and rosiglitazone regulate human cultured airway smooth muscle proliferation through different mechanisms, British Journal of Pharmacology, vol. 141, p. 517-525.

Wilen S.H. (1978-1984) Topics in Stereochemistry, Wiley-Interscience: NY, 1972, 6, 107 Eds. E.L. Eliel, N.L. Allinger; P.Newman, Optical resolution Procedures of Chiral Compounds 1-3, Resolution Information Center, NY.

Zhang H. et al. (2005) Collecting duct-specific deletion of peroxisome proliferator-activated receptor γ blocks thiazolidinedione-induced fluid retention, Proc. Natl. Acad. Sci. USA;102:9406-11.

FDA, label for Pioglitazone tablets, Aug. 2007, www.fda.gov/medwatch/SAFETY/2007/Sep_PI/Actoplus Met_PI.pdf.

IUPAC R-7.2.1.The R/S convention downloaded Nov. 26, 2010 http://www.acdlabs.com/iupac/nomenclature/93/r93_630.htm.

Avandia. FDA Label, May 25, 1999.

Honda, K. et al., "Peroxisome Proliferator-Activated Receptor Gamma is Expressed in Airways and Inhibits Features of Airway Remodeling in Mouse Asthma Model",J Allergy Clin Immunol, 113(5), pp. 882-888, 2004.

Jamali, B. et al., "Investigation of Racemisation of the Enantiomers of Glitazone Drug Compounds at Different pH Using Chiral HPLC and Chiral CE", Journal of Pharmaceutical and Biomedical Analysis, 46, pp. 82-87. 2008.

Cazzola et al., "Treating systemic effects of COPD", Trends in Pharmacological Sciences 28(10): 544-550 (Oct. 2, 2007), XP022282058.

Mueller et al., "Peroxisome proliferator-activated receptor gamma ligands attenuate immunological symptoms of experimental allergic asthma", Archives of Biochemistry and Biophysics 418(2): 186-196 (Oct. 15, 2003), XP004458908.

V. Narala et al., "Pioglitazone is as effective as dexamethasone in a cockroach allergen-induced murine model of asthma", Respiratory Research, Biomed. Central Ltd. 8(1): 1-10 (Dec. 4, 2007), XP021031353.

Y. Matsui et al., "Optically active thiazlidine derivative activating peroxisome proliferation factor receptor gamma for treating diabetes, hyperglycemia, is prepared by optically resolving racemic mixture of thiazolidine monohydrochloride", Database WPI Week 20085 Thomson Scientific, WO 2007/100027 (Sep. 7, 2007), pp. 1-3, XP002553092.

International Preliminary Report on Patentability dated Feb. 8, 2011 for PCT GB2009/001920.

Casarosa et al., "Functional and Biochemical Rationales for the 24-Hour-Long Duration of Action of Olodaterol", The Journal of Pharmacology and Experimental Therapeutics, 337(3):600-609 (2011).

Avandia, "EPAR Summary for the public", European Medicines Agency, pp. 2-3 (2010).

Aclidinium Bromide, Medchem Express, http://www.medchemexpress.com/product/Aclidinium-Bromide.html (2009).

Dr. Quick, "France and Germany Withdraw Use of Actos Because of Risk of Bladder Cancer", Health ProSunday, Jun. 12, 2011.

"European Medicines Agency recommends suspension of Avandia, Avandamet and Avaglim" European Medicines Agency (Sep. 23, 2010).

Welch et al., "Studies on the Racemization of a Stereolabile 5-Aryl-thiazolidinedione", Chirality, 15:143-147 (2003).

"Questions and answers on the review of pioglitazone-containing medicines (Actos, Glustin, Competact, Glubrava and Tandemact)" European Medicines Agency, pp. 1-3, (Jul. 21, 2011).

Jamali B et al., "Generic, highly selective and robust capillary electrophoresis method for separation of a racemic mixture of glitazone compounds", Journal of Chromatography A, 1049 (2004),183-187.

\* cited by examiner

RESPIRATORY DISEASE TREATMENT

RELATED APPLICATIONS

This application is a divisional of U.S. application Ser. No. 12/850,318, filed Aug. 4, 2010, which is a continuation-in-part of Great Britain Application No. 0913672.2, filed Aug. 5, 2009; and of International Application PCT/GB2009/001920, filed Aug. 5, 2009, which claims the benefit of priority of Great Britain Patent Application Nos. 0814488.3 and 0823568.1, filed Aug. 7, 2008 and Dec. 24, 2008, respectively, all of which are herein incorporated by reference by their entireties.

This invention relates to the use of the substantially pure 5R enantiomers of the known glitazone drug class, such as the known pharmaceutical products pioglitazone and rosiglitazone, for pulmonary administration by inhalation, for treatment of inflammatory respiratory diseases.

BACKGROUND TO THE INVENTION

A broad spectrum of respiratory diseases and disorders has been recognized, many of which have overlapping and interacting etiologies. Two of the most widespread and prevalent of these diseases are chronic obstructive pulmonary disease (COPD) and asthma. Respiratory diseases have a significant inflammatory component. For example, current therapy for COPD and severe asthma focuses mainly on the reduction of symptoms using short and long acting bronchodilators either as monotherapies or combinations of long acting $\beta_2$ agonist bronchodilators with inhaled corticosteroids (ICS). The disappointing anti-inflammatory data for ICS either alone or in combination with $\beta_2$ agonists has intensified the search for an effective anti-inflammatory drug for COPD. COPD is clearly a chronic inflammatory disorder that involves complex interactions between cells of the innate and acquired immune response both in the lung and potentially also systemically. One hypothesis under intense investigation is whether novel, demonstrably anti-inflammatory agents can halt or slow the functional decline characteristic of COPD. Reducing the frequency and severity of exacerbations has become an increasingly important target for COPD therapy as the prognosis for patients following exacerbations is poor. Anti-inflammatory therapy in COPD, and in asthma, is expected to reduce the frequency and severity of exacerbations. It is also desirable that decline in lung function and quality of life are also ameliorated with treatment.

Hence, new treatments for inflammatory respiratory diseases, including asthma, COPD, allergic airway syndrome, bronchitis, cystic fibrosis, emphysema and pulmonary fibrosis (including idiopathic pulmonary fibrosis), are constantly sought.

Peroxisome Proliferation Receptor gamma receptor (PPARγ) agonists are a class of drugs which increase sensitivity to glucose in diabetic patients. Physiological activation of PPARγ is believed to increase the sensitivity of peripheral tissues to insulin, thus facilitating the clearance of glucose from the blood and producing the desired anti-diabetic effect.

Many PPARγ agonists are known from the patent and other literature, but currently only two are approved for clinical use in diabetes; Rosiglitazone and Pioglitazone. See Campbell I W, *Curr Mol Med.* 2005 May; 5(3):349-63. Both of these compounds are thiazolidinediones ("TZDs" or "glitazones"), and are in practice administered by the oral route for systemic delivery.

In addition to its effect on glucose metabolism, a variety of reports have been published which demonstrate that rosiglitazone also exerts anti-inflammatory effects. For instance, (i) rosiglitazone has been reported to exert effects in diabetic patients consistent with an anti-inflammatory effect (Haffner et al., Circulation. 2002 Aug. 6; 106(6):679-84, Marx et al., Arterioscler. Thromb. Vasc. Biol. 2003 Feb. 1; 23(2):283-8); (ii) Rosiglitazone has been reported to exert anti-inflammatory effects in a range of animal models of inflammation, including: carageenan-induced paw oedema (Cuzzocrea et al., Eur. J. Pharmacol. 2004 Jan. 1; 483(1):79-93), TNBS-induced colitis (Desreumanux et al., J. Exp. Med. 2001 Apr. 2; 193(7):827-38, Sanchez-Hidalgo et al., Biochem. Pharmacol. 2005 Jun. 15; 69(12):1733-44), experimental encephalomyelitis (Feinstein et al., Ann. Neurol. 2002 June; 51(6):694-702) collagen-induced (Cuzzocrea et al., Arthritis Rheum. 2003 December; 48(12):3544-56) and adjuvant-induced arthritis (Shiojiri et al., Eur. J. Pharmacol. 2002 Jul. 19; 448 (2-3):231-8), carageenan-induced pleurisy (Cuzzocrea et al., Eur. J. Pharmacol. 2004 Jan. 1; 483(1):79-93), ovalbumin-induced lung inflammation (Lee et al., FASEB J. 2005 June; 19(8):1033-5) and LPS-induced lung tissue neutrophilia (Birrell et al., Eur. Respir. J. 2004 July; 24(1):18-23) and (iii) rosiglitazone has been reported to exert anti-inflammatory effects in isolated cells, including iNOS expression in murine macrophages (Reddy et al., Am. J. Physiol. Lung Cell. Mol. Physiol. 2004 March; 286(3):L613-9), TNFα-induced MMP-9 activity in human bronchial epithelial cells (Hetzel et al., Thorax. 2003 September; 58(9):778-83), human airway smooth muscle cell proliferation (Ward et al., Br. J. Pharmacol. 2004 February; 141(3):517-25) and MMP-9 release by neutrophils (WO 0062766). PPARγ agonists have also been shown to be effective in models of pulmonary fibrosis (Milam et al., Am. J. Physiol. Lung Cell. Mol. Physiol, 2008, 294(5): L891-901) and pulmonary arterial hypertension (Crossno et al., Am. J. Physiol. Lung Cell. Mol. Physiol, 2007, 292(4): L885-897).

Based on observations of anti-inflammatory activity in cells relevant to the lung, the utility of other PPARγ agonists has been suggested for the treatment of inflammatory respiratory disorders including asthma, COPD, cystic fibrosis and pulmonary fibrosis. See WO0053601, WO0213812 and WO0062766. These suggestions include administration by both the systemic oral and pulmonary inhalation routes.

Unfortunately, PPARγ agonists also have unwanted cardiovascular effects, including haemodilution, peripheral and pulmonary oedema and congestive heart failure (CHF). These effects are also believed to result from activation of PPARγ. In particular, a significant effort has been devoted to investigating the hypothesis that PPARγ agonists disturb the normal maintenance of fluid balance via binding to the PPARγ receptor in the kidney. See Guan et al, *Nat. Med.* 2005; 11(8):861-6 and Zhang et. al., *Pro.c Natl. Acad. Sci. USA.* 2005 28; 102 (26):9406-11. Treatment with PPARγ agonists by the oral route for systemic delivery is also associated with an unwanted increase in body weight.

COPD patients are known to be at a higher risk than other clinical populations from congestive heart failure (CHF) (Curkendall et al, Ann Epidemiol, 2006; 16: 63-70, Padeletti M et al, Int J Cardiol. 2008; 125(2):209-15) and so it is important that systemic activation of the PPARγ receptors is kept to a minimum in these patients to avoid increasing the likelihood of CHF being observed. Administering respiratory drugs by the inhaled route is one approach to target the lung with an anti-inflammatory agent whilst keeping systemic exposure of the drug low, thus reducing the likelihood of systemic activity and observation of side effects.

Pioglitazone has Structural Formula (I)

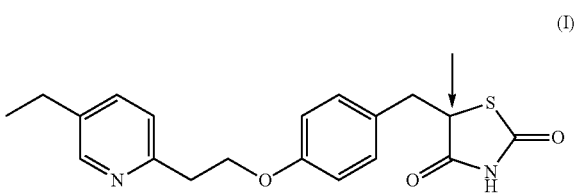 [SMILES: CCc1ccc(CCOc2ccc(CC3SC(=O)NC3=O)cc2)nc1]

(I)

and can be named as 5-{4-[2-(5-ethylpyridin-2-yl)ethoxy] benzyl}-1,3-thiazolidine-2,4-dione. The carbon atom in the 5-position of the thiazolidine-dione ring of pioglitazone, indicated by an arrow in formula (I) above, is asymmetric, so pioglitazone has two enantiomers, the 5R and 5S enantiomers.

Rosiglitazone has the structural formula (II) and can be named as 5-(4-{2-[methyl (pyridin-2-yl)amino]ethoxy]benzyl}-1,3-thiazolidine-2,4-dione. The carbon atom in the 5-position of the thiazolidine-dione ring of rosiglitazone, indicated by an arrow in formula (II) below, is also asymmetric, so rosiglitazone also has two enantiomers, the 5R and 5S enantiomers.

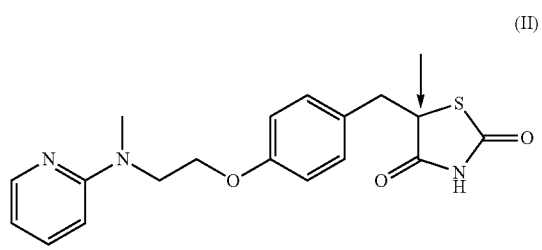 [SMILES: CN(CCOc1ccc(CC2SC(=O)NC2=O)cc1)c1ccccn1]

(II)

The 5S enantiomer of rosiglitazone has a higher binding affinity for the PPARγ receptor than the 5R enantiomer (30 nM vs 2 μM, Parks et al., 1998, Bioorg. Med. Chem. Lett. 8(24):3657-8). For another member of the glitazone class, Rivoglitazone, the 5S enantiomer also has higher receptor binding affinity than the 5R enantiomer (see page 13 of WO2007100027).

In practice, pioglitazone and rosiglitazone are administered for treatment of diabetes as a mixture of 5R and 5S enantiomers (a 1:1 racemic mixture) by the oral route for systemic delivery. The individual enantiomers of these compounds, and members of the glitazone family generally, are known to equilibrate rapidly in vivo after oral administration (see for example *J. Clin. Pharmacol.* 2007, 47, 323-33; *Rapid Commun. Mass Spectrom.* 2005, 19, 1125-9; *J. Chromatography*, 835 (2006), 40-46; *Biopharmaceutics and Drug Disposition* 1997, 18 (4), 305-24; *Chem. Pharm. Bull* 1984, 32, (11) 4460-65; T. *J. Med. Chem.* 1991, 34, 319-25) so there is no difference in practice between oral administration of either substantially pure isomer and oral administration of the racemic mixture. Specifically in relation to pioglitazone, it has been stated in a submission to the Federal Drug Administration (FDA) that there was no difference in activity following oral administration either of the racemate or the individual enantiomers in a rodent diabetes model (www.fda.gov/medwatch/SAFETY/2007/Sep_PI/Actoplus Met_PI.pdf):

"(Pioglitazone) contains one asymmetric carbon, and the compound is synthesized and used as the racemic mixture. The two enantiomers of pioglitazone interconvert in vivo. No differences were found in the pharmacologic activity between the two enantiomers".

The effects of pulmonary inhalation of rosiglitazone or pioglitazone (or indeed any other glitazone) in either racemic or single enantiomer form do not appear to have been studied. It appears that nothing has been published concerning the potential equilibration of the 5R and 5S enantiomers of either compound, or any other glitazone, when contacted directly with lung tissue.

The glitazone class of PPARγ agonists as a whole is characterised by the presence in the molecule of a thiazolidin-2, 4-dione radical (A), often as part of a (thiazolidin-2,4,dione-5-yl)methylphenyl radical (B):

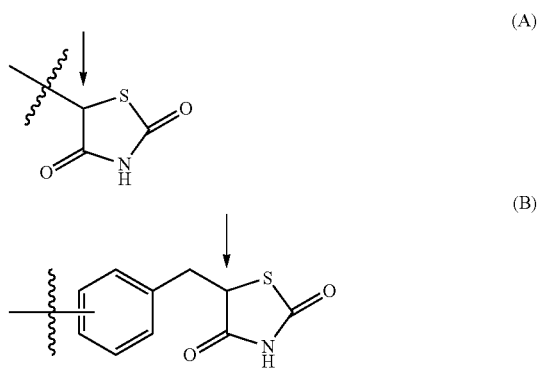

(A)

(B)

and the ring carbon atom indicated by the arrow is numbered as the 5-position of the thiazolidinone ring. The term "glitazone" as used herein refers to a PPARγ agonist compound whose structure includes a thiazolidin-2,4-dione radical (A), or a (thiazolidin-2,4,dione-5-yl)methylphenyl radical (B):

Besides the approved and marketed rosiglitazone and pioglitazone, there is a multitude of glitazones known from the patent and scientific literature. Known examples include the following:

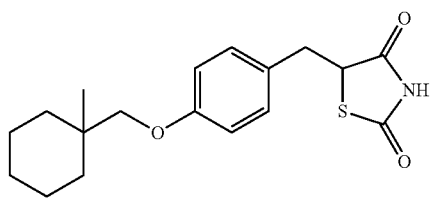

Ciglitazone

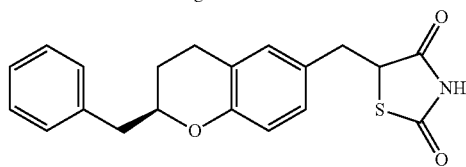

Englitazone

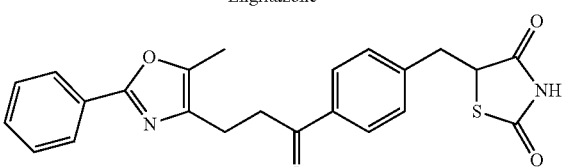

Darglitazone

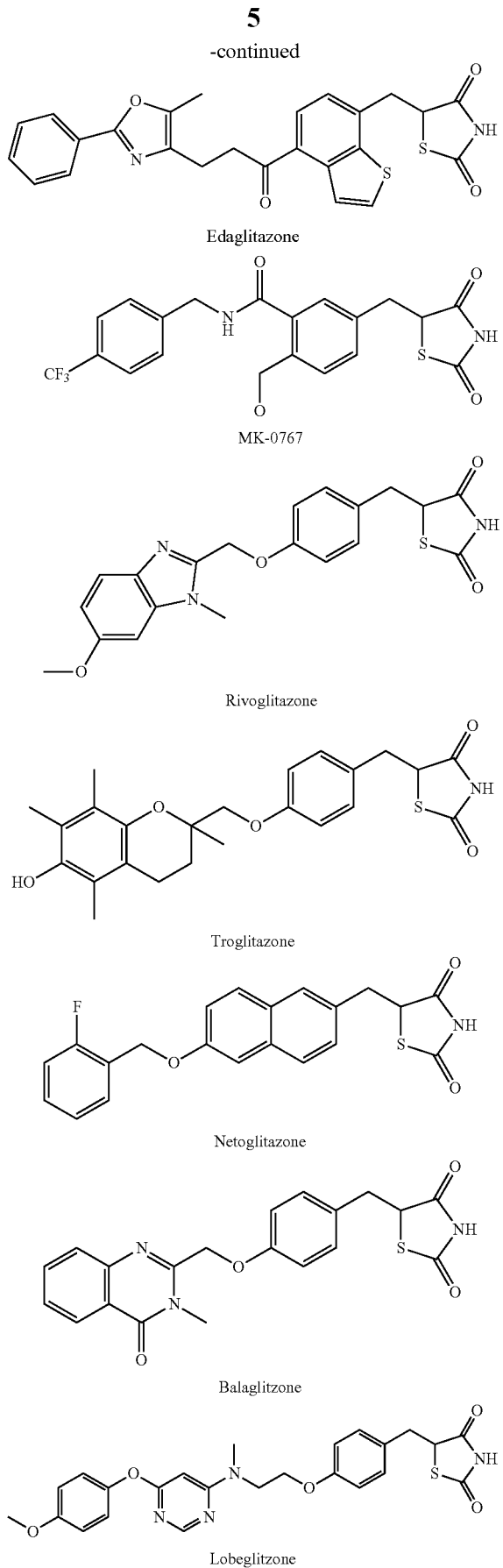

Edaglitazone

MK-0767

Rivoglitazone

Troglitazone

Netoglitazone

Balaglitzone

Lobeglitzone

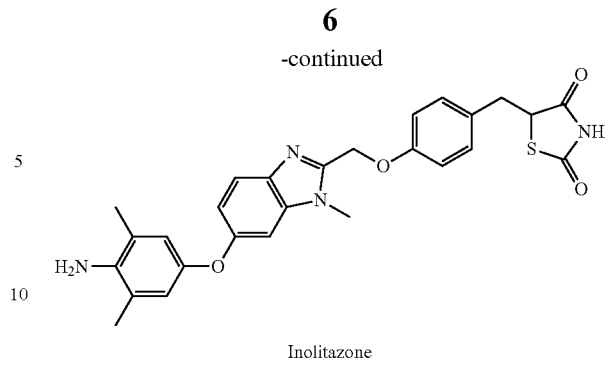

Inolitazone

BRIEF SUMMARY OF THE INVENTION

This invention is based on the finding that, for treatment of inflammatory respiratory disease by inhalation, the 5R-enantiomer of a glitazone is more effective than the 5S enantiomer. Proof of principle drives from an animal model of treatment of inflammatory respiratory disease by inhalation, in which the 5R-enantiomers of pioglitazone and rosiglitazone have been shown to be active, whereas the 5S enantiomers were essentially inactive. This finding leads to the conclusion that inhaled pulmonary administration of the 5R enantiomer of a glitazone, in particular the 5R-enantiomer of pioglitazone or rosiglitazone, allows the anti-inflammatory effect of the compound to be achieved more efficiently than by similar administration of the racemate, with all the concomitant reduced side effect benefits of lower systemic exposure than oral administration.

DETAILED DESCRIPTION OF THE INVENTION

Figure 1:
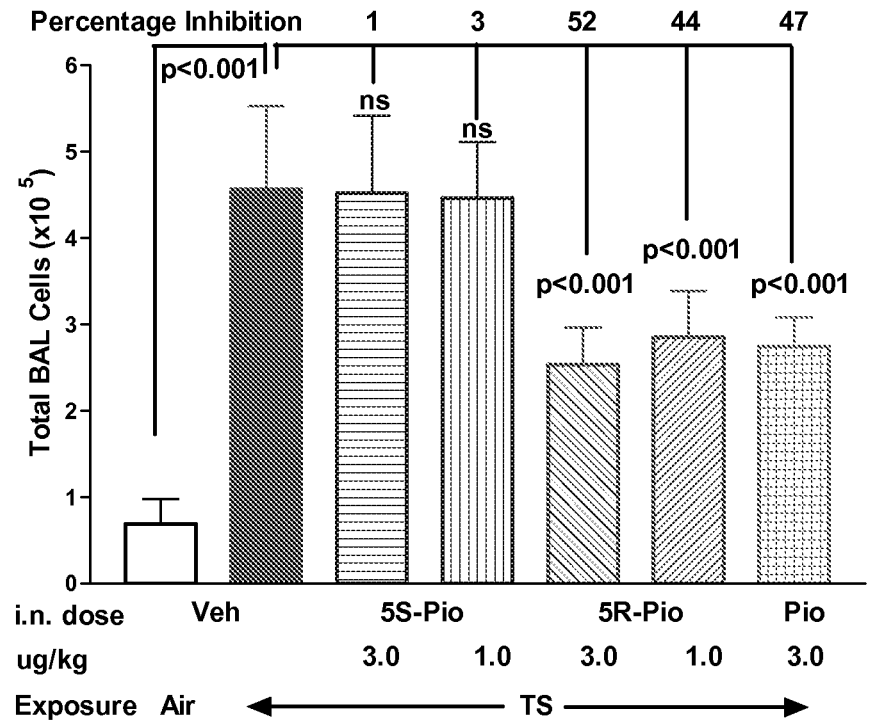
FIG. 1 is a bar graph that illustrates the effect of intranasal administration to laboratory mice with vehicle (0.2% tween 80 in saline), 5S-pioglitazone (1 or 3 µg/kg), 5R-pioglitazone (1 or 3 µg/kg), or racemic pioglitazone (3 µg/kg) on the number of BAL cells induced by tobacco smoke 24 hours post the final exposure.

As used herein, the term "glitazone" has the meaning ascribed to it above, i.e., a PPARγ agonist compound whose structure includes a thiazolidin-2,4-dione radical (A), or a (thiazolidin-2,4,dione-5-yl)methylphenyl radical (B):

As used herein the term "pioglitazone" or "pioglitazone component" means the compound 5-{4-[2-(5-ethylpyridin-2-yl)ethoxy]benzyl}-1,3-thiazolidine-2,4-dione of formula (I) above, or a pharmaceutically acceptable salt thereof.

As used herein the term "rosiglitazone" or "rosiglitazone component" means the compound 5-(4-{2-[methyl(pyridin-2-yl)amino]ethoxy]benzyl}-1,3-thiazolidine-2,4-dione of formula (II) above, or a pharmaceutically acceptable salt thereof.

As used herein, the term "enantiomeric excess" or its abbreviation "e.e." is defined as the percentage:

$$((R-S)/(R+S)) \times 100 \text{ percent}$$

where R and S are the respective weight fractions of the R and S enantiomers in a sample. Thus for a glitazone sample containing 95% by weight of the 5R enantiomer and 5% of the 5S enantiomer, the enantiomeric excess of R over S enantiomer is $((95-5)/95+5)) \times 100 = 90\%$ As used herein, the term "diastereomeric excess" or its abbreviation "d.e." as applied to a chiral salt of pioglitazone and an enantiomer is defined as the percentage:

$$((R-S)/(R+S)) \times 100 \text{ percent}$$

where R and S are the respective weight fractions of the salt diastereomer having the R-pioglitazone configuration and S-pioglitazone configurations in a sample. Thus for a pioglitazone O,O'-dibenzoyl-L-tartrate wherein the content by weight of pioglitazone consists of at least 95% by weight of the 5R enantiomer and less than 5% of the 5S enantiomer, the diastereomeric excess of R over S diastereomer is $((95-5)/95+5)) \times 100 = 90\%$.

In one aspect, the present invention provides a pharmaceutical composition adapted for pulmonary administration by inhalation, which composition comprises a glitazone, particularly pioglitazone or rosiglitazone, and one or more pharmaceutically acceptable carriers and/or excipients, wherein the glitazone content of the composition consists of at least 95% by weight of the 5R enantiomer and less than 5% of the 5S enantiomer.

In another aspect, the invention provides a glitazone, for example pioglitazone or rosiglitazone, for use in the treatment of inflammatory respiratory disease by pulmonary administration by inhalation, wherein the glitazone inhaled consists of at least 95% by weight of the 5R enantiomer and less than 5% of the 5S enantiomer In another aspect, the invention provides the use of a glitazone, for example pioglitazone or rosiglitazone, in the preparation of a medicament for the treatment of inflammatory respiratory disease by pulmonary administration by inhalation, wherein the glitazone content of the medicament consists of at least 95% by weight of the 5R enantiomer and less than 5% of the 5S enantiomer.

In another aspect, the invention provides a method of treatment of inflammatory respiratory disease comprising pulmonary administration of a therapeutically effective amount of a glitazone, for example pioglitazone or rosiglitazone, to a subject suffering such disease by inhalation, wherein the glitazone inhaled consists of at least 95% by weight of the 5R enantiomer and less than 5% of the 5S enantiomer.

In all aspects of the invention, the glitazone component, for example the pioglitazone or rosiglitazone component, may be inhaled via the nose or the mouth. Preferably it is inhaled via the mouth.

In all aspects of the invention, the glitazone component, for example pioglitazone or rosiglitazone, should preferably contain as little of the 5S enantiomer as possible. For example, the 5R enantiomer may constitute at least 97%, or at least 98%, or at least 99% by weight of the glitazone component.

In all aspects of the invention, the glitazone component, for example the pioglitazone or rosiglitazone component, may be accompanied by, or administered sequentially or concurrently with, one or more respiratory disorder treatment agents useful for the purpose of preventing and treating respiratory disorders, other than a PPARγ agonist.

In all aspects of the invention, currently the most preferred glitazone component is pioglitazone.

In all aspects of the invention, the wherein the inflammatory respiratory disease may be selected from, for example, mild asthma, moderate asthma, severe asthma, steroid resistant asthma, bronchitis, chronic obstructive pulmonary disease (COPD), cystic fibrosis, pulmonary edema, pulmonary embolism, pneumonia, pulmonary sarcoisosis, silicosis, pulmonary fibrosis, respiratory failure, acute respiratory distress syndrome, emphysema, chronic bronchitis, tuberculosis, and lung cancer.

The glitazone component can be in the form of a pharmaceutically acceptable salt. The term "pharmaceutically acceptable salt" refers to salts prepared from pharmaceutically acceptable inorganic and organic acids and bases.

Pharmaceutically acceptable inorganic bases include metallic ions. More preferred metallic ions include, but are not limited to, appropriate alkali metal salts, alkaline earth metal salts and other physiological acceptable metal ions. Salts derived from inorganic bases include aluminum, ammonium, calcium, copper, ferric, ferrous, lithium, magnesium, manganic salts, manganous, potassium, sodium, zinc, and the like and in their usual valences. Exemplary salts include aluminum, calcium, lithium, magnesium, potassium, sodium and zinc. Particularly preferred are the ammonium, calcium, magnesium, potassium, and sodium salts.

Salts derived from pharmaceutically acceptable organic non-toxic bases include salts of primary, secondary, and tertiary amines, including in part, trimethylamine, diethylamine, N,N'-dibenzylethylenediamine, chloroprocaine, choline, diethanolamine, ethylenediamine, meglumine (N-methylglucamine) and procaine; substituted amines including naturally occurring substituted amines; cyclic amines; and quaternary ammonium cations. Examples of such bases include arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

Illustrative pharmaceutically acceptable acid addition salts of the compounds of the present invention can be prepared from the following acids, including, without limitation formic, acetic, propionic, benzoic, succinic, glycolic, gluconic, lactic, maleic, malic, tartaric, citric, nitric, ascorbic, glucuronic, maleic, fumaric, pyruvic, aspartic, glutamic, benzoic, hydrochloric, hydrobromic, hydroiodic, isocitric, xinafoic, tartaric, trifluoroacetic, pamoic, propionic, anthranilic, mesylic, napadisylate, oxalacetic, oleic, stearic, salicylic, p-hydroxybenzoic, nicotinic, phenylacetic, mandelic, embonic (pamoic), methanesulfonic, phosphoric, phosphonic, ethanesulfonic, benzenesulfonic, pantothenic, toluenesulfonic, 2-hydroxyethanesulfonic, sulfanilic, sulfuric, salicylic, cyclohexylaminosulfonic, algenic, β-hydroxybutyric, galactaric and galacturonic acids. Exemplary pharmaceutically acceptable salts include the salts of hydrochloric acid and hydrobromic acid.

Compositions of the invention are useful for treatment of inflammatory respiratory disorders, for example asthma (mild, moderate or severe), e.g., bronchial, allergic, intrinsic, extrinsic, exercise-induced, drug-induced (including aspirin and NSAID-induced) and dust-induced asthma, steroid resistant asthma, bronchitis including infectious and eosinophilic bronchitis, chronic obstructive pulmonary disease (COPD), cystic fibrosis, pulmonary fibrosis including cryptogenic fibrosing alveolitis, idiopathic pulmonary fibrosis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension (including pulmonary arterial hypertension); antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus, pulmonary edema, pulmonary embolism, pneumonia, pulmonary sarcoidosis, silicosis, farmer's lung and related diseases; hypersensitivity pneumonitis, respiratory failure, acute respiratory distress syndrome, emphysema, chronic bronchitis, tuberculosis, and lung cancer. In particular, the methods and compositions of the present invention encompass the prevention and treatment of the respiratory disorder, COPD.

As used herein, the term "chronic obstructive pulmonary disease" or "COPD" refers to a set of physiological symptoms including chronic bronchitis, chronic cough, expectoration, exertional dyspnea and a significant, progressive reduction in airflow that may or may not be partly reversible. Emphysema may also be present in the lungs. COPD is a disease characterized by a progressive airflow limitation caused by an abnormal inflammatory reaction to the chronic inhalation of particles.

In subjects with the disorder, poor gas exchange in the lungs leads to decreased oxygen levels in the blood, increased levels of carbon dioxide and shortness of breath. Chronic airflow obstruction in COPD is complicated by the loss of lung elasticity resulting from enzymatic destruction of the lung parenchyma. Rather than a single pathologic condition, COPD is an umbrella term encompassing chronic obstructive bronchitis and emphysema.

Compositions suitable for administration by inhalation via the mouth or the nose are known, and may include carriers and/or diluents that are known for use in such compositions. The composition may contain 0.01-99% by weight of the pioglitazone or rosiglitazone component. Preferably, a unit dose comprises the pioglitazone or rosiglitazone component in an amount of 1 µg to 50 mg.

The most suitable dosage level may be determined by any suitable method known to one skilled in the art. It will be understood, however, that the specific amount for any particular patient will depend upon a variety of factors, including the activity of the specific compound that is used, the age, body weight, diet, general health and sex of the patient, time of administration, the route of administration, the rate of excretion, the use of any other drugs, and the severity of the disease undergoing treatment. Optimum dosages will be determined by clinical trial, as is required in the art.

Compositions of the invention may be used in combination with other drugs that are used in the treatment/prevention/suppression or amelioration of the diseases or conditions for which present compounds are useful. Such other drugs may be administered, by a route and in an amount commonly used therefore, contemporaneously or sequentially with the glitazone component, particularly the pioglitazone or rosiglitazone component. When a compound of the invention is used contemporaneously with one or more other drugs, a pharmaceutical composition containing such other drugs in addition to the pioglitazone component is preferred. Accordingly, the pharmaceutical compositions of the present invention include those that also contain one or more other active ingredients, in addition to the glitazone component, particularly the pioglitazone or rosiglitazone component.

Suitable therapeutic agents for a combination therapy with the glitazone compositions, particularly the pioglitazone or rosiglitazone compositions, of the invention include: (1) a steroid drug such as a corticosteroid, for example beclomethasone, (e.g., as the mono or the dipropionate ester), flunisolide, fluticasone (e.g., as the propionate or furoate ester), ciclesonide, mometasone (e.g., as the furoate ester), mometasone desonide, rofleponide, hydrocortisone, prednisone, prednisolone, methyl prednisolone, naflocort, deflazacort, halopredone acetate, fluocinolone acetonide, fluocinonide, clocortolone, tipredane, prednicarbate, alclometasone dipropionate, halometasone, rimexolone, deprodone propionate, triamcinolone, betamethasone, fludrocori?tisone, desoxycorticosterone, etiprednol dicloacetate and the like. Steroid drugs can additionally include steroids in clinical or pre-clinical development for respiratory diseases such as GW-685698, GW-799943, GSK 870086, QAE397, NCX-1010, NCX-1020, NO-dexamethasone, PL-2146, NS-126 (formerly ST-126) and compounds referred to in international patent applications WO0212265, WO0212266, WO02100879, W003062259, W003048181 and W003042229. Steroid drugs can also additionally include next generation molecules in development with reduced side effect profiles such as selective glucocorticoid receptor agonists (SEGRAs), including ZK-216348 and compounds referred to in international patent applications WO-00032585, WO-000210143, WO-2005034939, WO-2005003098, WO-2005035518 and WO-2005035502 and functional equivalents and functional derivatives thereof; (2) a β2-adrenoreceptor agonist, such as albuterol, bambuterol, terbutaline, fenoterol, formoterol, formoterol fumarate, salmeterol, salmeterol xinafoate, arformoterol, arfomoterol tartrate, indacaterol (QAB-149), carmoterol, picumeterol, BI 1744 CL, GSK159797, GSK59790, GSK159802, GSK642444, GSK678007, GSK96108, clenbuterol, procaterol, bitolterol, and brodxaterol, TA-2005 and also compounds of EP1440966, JP05025045, WO93/18007, WO99/64035, US2002/0055651, US2005/0133417, US2005/5159448, WO00/075114, WO01/42193, WO01/83462, WO02/66422, WO02/70490, WO02/76933, WO03/24439, WO03/42160, WO03/42164, WO03/72539, WO03/91204, WO03/99764, WO04/16578, WO04/016601, WO04/22547, WO04/32921, WO04/33412, WO04/37768, WO04/37773, WO04/37807, WO0439762, WO04/39766, WO04/45618, WO04/46083, WO04/71388, WO04/80964, EP1460064, WO04/087142, WO04/89892, EP01477167, US2004/0242622, US2004/0229904, WO04/108675, WO04/108676, WO05/033121, WO05/040103, WO05/044787, WO04/071388, WO05/058299, WO05/058867, WO05/065650, WO05/066140, WO05/070908, WO05/092840, WO05/092841, WO05/092860, WO05/092887, WO05/092861, WO05/090288, WO05/092087, WO05/

080324, WO05/080313, US20050182091, US20050171147, WO05/092870, WO05/077361, DE10258695, WO05/111002, WO05/111005, WO05/110990, US2005/0272769 WO05/110359, WO05/121065, US2006/0019991, WO06/016245, WO06/014704, WO06/031556, WO06/032627, US2006/0106075, US2006/0106213, WO06/051373, WO06/056471, WO08/096112, WO08/104790, WO08/096119, WO08/096112; (3) a leukotriene modulator, for example, montelukast or pranlukast; (4) anticholinergic agents, for example, selective muscarinic-3 (M3) receptor antagonists such as ipratropium bromide, tiotropium, tiotropium bromide (Spiriva®), glycopyrollate, NVA237, LAS34273, GSK656398, GSK233705, GSK 573719, LAS35201, QAT370 and oxytropium bromide; (5) phosphodiesterase-IV (PDE-IV) inhibitors, for example, roflumilast or cilomilast; (6) an antitussive agent, such as codeine or dextramorphan; (7) a non-steroidal anti-inflammatory agent (NSAID), for example, ibuprofen or ketoprofen; (8) a mucolytic, for example, N acetyl cysteine or fudostein; (9) a expectorant/mucokinetic modulator, for example, ambroxol, hypertonic solutions (e.g., saline or mannitol) or surfactant; (10) a peptide mucolytic, for example, recombinant human deoxyribonuclease I (dornase-alfa and rhDNase) or helicidin; (11) antibiotics, for example, azithromycin, tobramycin and aztreonam; and (12) p38 MAP kinase inhibitors such as GSK 856553 and GSK 681323.

In one aspect, the invention provides for the use of inhaled administration of the glitazone compositions, particularly the pioglitazone or rosiglitazone compositions, of the invention in combination with other anti-inflammatory drugs and bronchodilator drug combinations (i.e. triple combination product), including but not limited to salmeterol xinafoate/fluticasone propionate (Advair/Seretide®), formoterol fumarate/budesonide (Symbicort®), formoterol fumarate/mometasone furoate, formoterol fumarate/beclometasone dipropionate (Foster®), formoterol fumarate/fluticasone propionate (FlutiForm®), Indacaterol/mometasone furoate, Indacaterol/QAE-397, GSK159797/GSK 685698, GSK159802/GSK 685698, GSK642444/GSK 685698, formoterol fumarate/ciclesonide, arformoterol tartrate/ciclesonide.

In another aspect, the invention provides for the use of inhaled administration of the glitazone compositions, particularly the pioglitazone or rosiglitazone compositions, of the invention in combination with other bronchodilator drug combinations, particularly B2 agonist/M3 antagonist combinations (i.e. triple combination product), including but not limited to salmeterol xinafoate/tiotropium bromide, formoterol fumarate/tiotropium bromide, BI 1744 CL/tiotropium bromide, indacaterol/NVA237, indacterol/QAT-370, formoterol/LAS34273, GSK159797/GSK 573719, GSK159802/GSK 573719, GSK642444/GSK 573719, GSK159797/GSK 233705, GSK159802/GSK 233705, GSK642444/GSK 233705, and compounds which possess both β2 agonist and M3 antagonist activity in the same molecule (dual functionality) such as GSK 961081.

Thus in another aspect, the invention provides a kit for treatment of respiratory disorders in a subject, the kit comprising one dosage form comprising a composition adapted for pulmonary administration by inhalation, which composition comprises a glitazone, particularly pioglitazone or rosiglitazone, and one or more pharmaceutically acceptable carriers and/or excipients, wherein the glitazone content of the composition consists of at least 95% by weight of the 5R enantiomer and less than 5% of the 5S enantiomer, and a second dosage form comprising another therapeutic agent, for example as discussed above, selected from anti-inflammatory agents, bronchodilators, mucolytic agents, antitussive agents, leukotriene inhibitors, and antibiotics.

For delivery by inhalation, the active compound is preferably in the form of microparticles. These may be prepared by a variety of techniques, including spray-drying, freeze-drying and micronisation. Following size reduction to produce microparticles, particle size distribution (PSD) of the compound is examined and generally described in the art by specifying d10, d50 and d90 values. The average particle size, i.e. the average equivalent diameter, is defined as the diameter where 50 mass-% (of the particles) of the powder have a larger equivalent diameter, and the other 50 mass-% have a smaller equivalent diameter. Hence the average particle size is denoted as equivalent d50. For inhaled use a d50 of less than 10 microns, preferably less than 5 microns is desired.

By way of example, a composition of the invention may be prepared as a suspension for delivery from a nebuliser or as an aerosol in a liquid propellant, for example for use in a pressurised metered dose inhaler (PMDI). Propellants suitable for use in a PMDI are known to the skilled person, and include CFC-12, HFA-134a, HFA-227, HCFC-22 ($CCl_2F_2$) and HFA-152 ($CH_4F_2$ and isobutane).

In a preferred embodiment of the invention, a composition of the invention is in dry powder form, for delivery using a dry powder inhaler (DPI). Many types of DPI are known.

Microparticles for delivery by inhalation may be formulated with excipients that aid delivery and release. For example, in a dry powder formulation, microparticles may be formulated with large carrier particles that aid flow from the DPI into the lung. Suitable carrier particles are known, and include lactose particles; they may have a mass median aerodynamic diameter of greater than 90 μm.

Aerosol generation can be carried out using, for example, pressure-driven jet atomizers or ultrasonic atomizers, preferably using propellant-driven metered aerosols or propellant-free administration of micronized active compounds from, for example, inhalation capsules or other "dry powder" delivery systems.

The compositions may be dosed as described depending on the inhaler system used. In addition to the active compounds, the administration forms may additionally contain excipients, such as, for example, propellants (e.g., Frigen in the case of metered aerosols), surface-active substances, emulsifiers, stabilizers, preservatives, flavourings, fillers (e.g. lactose in the case of powder inhalers) or, if appropriate, further active compounds.

For the purposes of inhalation, a large number of systems are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhalers for example as described in EP-A-0505321).

Methods of Preparation of Glitazone Enantiomers

Glitazones can be separated on a small scale using chiral HPLC (see for example Methods 1-3 and 5-7 of the Chemical Examples Section below). Chiral columns include CHIRALPAK AD, AD-H, AS-V, 50801, IA, IC, OD, OF, OG, OJ, OK, and OZ. Preferred chiral columns for HPLC are CHIRALPAK AD-H and CHIRALPAK IA using elution with ethanol and varying portions of TFA, preferably 0.05-0.2% TFA.

For large scale separation of enantiomers to produce quantities typical of commercial pharmaceutical production, several known general methods are potentially available, but the success of any of the known methods for reliable and efficient separation of a given racemate is unpredictable. In the case of some racemic compounds, identifying an efficient large scale resolution method is not easy. Resolution of racemic pioglitazone on a large scale proved to be problematic, as the Process Development Examples below show. However, a successful resolution method for pioglitazone was developed, which may be used on small or large scales, and that method forms part of the invention.

Thus, according to this aspect of the invention, there is provided a method for the preparation of pioglitazone O,O'-dibenzoyl-L-tartrate wherein the content by weight of pioglitazone consists of at least 95% by weight of the 5R enantiomer and less than 5% of the 5S enantiomer, which method comprises:

(1a) adding seed crystals of 5R-pioglitazone O,O'-dibenzoyl-L-tartrate to a methanol-water solution of racemic pioglitazone hydrochloride and O,O'-dibenzoyl-L-tartaric acid, thereby precipitating pioglitazone O,O'-dibenzoyl-L-tartrate;

(1b) recovering said precipitate from step (1a);

(1c) forming a solution of the precipitate from step (1b) in a solvent mixture of methanol, acid and water and mixing into the resultant solution seed crystals of 5R-pioglitazone O,O'-dibenzoyl-L-tartrate, thereby precipitating pioglitazone O,O'-dibenzoyl-L-tartrate;

(1d) recovering said precipitate from step (1c);

(1e) repeating steps (1c) and (1d), the recovered product being the desired pioglitazone O,O'-dibenzoyl tartrate wherein the content by weight of pioglitazone consists of at least 95% by weight of the 5R enantiomer and less than 5% of the 5S enantiomer.

The 5R enantiomeric content of the pioglitazone part of the pioglitazone O,O'-dibenzoyl-L-tartrate precipitate at step (1d) is higher than that at step (1b), and the 5R enantiomeric content of the pioglitazone part of the pioglitazone O,O'-dibenzoyl-L-tartrate precipitate at step (1e) is 95% by weight or more, as is the object if the invention.

The seed crystals of 5R-pioglitazone (−)-O,O'-dibenzoyl-L-tartrate used in steps (1a) and (1c) may be obtained by the method described in the Preliminary Example below, in those seed crystals, the content by weight of pioglitazone preferably consists of at least 95% by weight of the 5R enantiomer and less than 5% of the 5S enantiomer, Step (1(e) of the above method may be omitted if the pioglitazone O,O'-dibenzoyl-L-tartrate recovered in step (1b) has a sufficiently high d.e. of R over S, for example a d.e of from about 60% to about 72%. A modification of the method which allows omission of step 1(e) comprises:

(2a) adding seed crystals of 5R-pioglitazone O,O'-dibenzoyl-L-tartrate to a methanol-water solution of racemic pioglitazone hydrochloride and O,O'-dibenzoyl-L-tartaric acid, thereby precipitating pioglitazone O,O'-dibenzoyl-L-tartrate, with gradual addition of more water such that the final volume ratio of water to methanol is in the range 0.8:1 to 1.2:1, and wherein the molar ratio of O,O'-dibenzoyl-L-tartaric acid:pioglitazone hydrochloride is in the range 0.5:1 to 1:1, preferably 0.5-0.8:1, such as about 0.6:1;

(2b) recovering said precipitate from step (2a);

(2c) forming a solution of the precipitate from step (2b) in a solvent mixture of methanol, acid and water and mixing into the resultant solution seed crystals of 5R-pioglitazone O,O'-dibenzoyl-L-tartrate, with gradual addition of more water such that the final volume ratio of water to methanol is in the range 0.8:1 to 1.2:1, thereby precipitating pioglitazone O,O'-dibenzoyl-L-tartrate;

(2d) recovering said precipitate from step (2c), the recovered product being the desired pioglitazone O,O'-dibenzoyl tartrate wherein the content by weight of pioglitazone consists of at least 95% by weight of the 5R enantiomer and less than 5% of the 5S enantiomer.

The acid whose presence is required in step 1(c) or 2(c) is preferably hydrochloric acid, but other acids which may be used include sulphuric, hydrobromic, trifluoroacetic, citric, dibenzoyl tartaric, malic, maleic, ditoluoyl tartaric and nitric acids. The presence of this acid appears to be essential for the stability of the pioglitazone-chiral resolving agent salt in the solution, to avoid precipitation of the pioglitazone free base.

An additional step may be included whereby the recovered pioglitazone O—O' dibenzoyl tartrate wherein the content by weight of pioglitazone consists of at least 95% by weight of the 5R enantiomer and less than 5% of the 5S enantiomer is converted by salt exchange into the hydrochloride salt or any other pharmaceutically acceptable salt such as hydrobromide, tosylate, L-tartrate, (−)—O,O'-dibenzoyl-L-tartrate, phosphate, hydroxy-ethanesulfonic acid and the naphthalene-1,5-disulfonic acid salts thereof, wherein the naphthalene-1,5-disulfonic acid salt contains two molecules of pioglitazone for each molecule of naphthalene-1,5-disulfonic acid. For example, the recovered 5-R pioglitazone O,O'-dibenzoyl tartrate may be dissolved in a solvent mixture of methanol or ethanol and hydrochloric acid, and the desired 5R-pioglitazone hydrochloride wherein the content by weight of pioglitazone consists of at least 95% by weight of the 5R enantiomer and less than 5% of the 5S enantiomer may be recovered from solution, if necessary by the addition of a counter-solvent such as ethyl acetate or diethyl ether. Salt exchange to the hydrochloride salt is preferably carried out in the presence of seed crystals of 5R-pioglitazone hydrochloride, prepared for example by the method of the Preliminary Example, step c.

The following Examples illustrate the preparation of pioglitazone and rosiglitazone enantiomers, and the biological results on which the present invention is based:

CHEMICAL EXAMPLES

General Experimental Details

Abbreviations used in the experimental section: c=concentration; h=hour; $H_2O$=distilled water; HPLC=high performance liquid chromatography; LCMS=liquid chromatography mass spectrometry; MeOH=methanol; TFA=trifluoroacetic acid; DMSO=dimethyl sulphoxide; HCl=hydrogen chloride; EtOH=ethanol; IPA=isopropyl alcohol; EtOAc=ethyl acetate; THF=tetrahydrofuran; $NH_4Cl$=ammonium chloride; LDA=lithium diisopropylamide; min=minutes; RT=room temperature; Rt=retention time; e.e.=enantiomeric excess; MP-Carbonate=macroporous triethylammonium methylpolystyrene carbonate (0.5% inorganic antistatic agent). d.e.=diastereomeric excess; SL-W003-2=(S)-1-[(S)-2-(2i-diphenylphosphinophenyl)ferrocenyl]ethyldicyclohexyl phosphine; $Rh(COD)_2BF_4$=bis(1,5-cyclooctadiene) Rhodium I tetrafluoroborate; pioglitazone=5-{4-[2-(5-ethylpyridin-2-yl)ethoxy]benzyl}-1,3-thiazolidine-2,4-dione; L-DBTA=L-dibenzoyl tartaric acid The nomenclature of structures was assigned using ACD Labs version 10.

NMR spectra were obtained on a Varian Unity Inova 400 spectrometer with a 5 mm inverse detection triple resonance probe operating at 400 MHz or on a Bruker Avance DRX 400 spectrometer with a 5 mm inverse detection triple resonance TXI probe operating at 400 MHz or on a Bruker Avance DPX 300 spectrometer with a standard 5 mm dual frequency probe operating at 300 MHz. Shifts are given in ppm relative to tetramethylsilane. Optical rotations were measured using an AA-10R automatic polarimeter with 5×25 mm jacketed sample cell. Asymmetric hydrogenolysis experiments were performed using Biotage Endeavor hydrogenation equipment.

All solvents and commercial reagents were used as received.

The Liquid Chromatography Mass Spectroscopy (LC/MS) and Liquid

Chromatography systems used:

Method 1

CHIRALPAK AD-H (250×30 mm, 5 µm), elution with EtOH+0.05% TFA—flow rate 30 ml/min. Detection—In-line UV detection set at 250 nM wavelength Method 2

CHIRALPAK 1A (250×4.6 mm, 5 µM), elution with EtOH+0.05% TFA—flow rate 0.7 ml/min. Detection—In-line DAD set at 280 nM wavelength Method 3

CHIRALCEL OD-RH (150×4.6 mm), elution with 90% MeOH+10% $H_2O$—flow rate 0.5 ml/min. Detection—In-line UV detection set at 254 nM wavelength Method 4

Waters Micromass ZQ2000 with a C18-reverse-phase column (100×3.0 mm Higgins Clipeus with 5 µm particle size), elution with A: water+0.1% formic acid; B: acetonitrile+0.1% formic acid. Gradient:

| Gradient - Time | flow mL/min | % A | % B |
|---|---|---|---|
| 0.00 | 1.0 | 95 | 5 |
| 1.00 | 1.0 | 95 | 5 |
| 15.00 | 1.0 | 5 | 95 |
| 20.00 | 1.0 | 5 | 95 |
| 22.00 | 1.0 | 95 | 5 |
| 25.00 | 1.0 | 95 | 5 |

Detection—MS, ELS, UV (100 µl split to MS with in-line UV detector). MS ionisation method—Electrospray (positive ion)

Method 5

CHIRALPAK IA (250×21 mm, 5 µm), elution with ethanol+0.2% TFA—flow rate 13 ml/min. Detection—In-line UV detection set at 220 nM wavelength Method 6

Chiral-AGP (150×4.0 mm, 5 µM), elution with A: 86% 10 mM potassium dihydrogen phosphate buffer pH 7.0; B: 14% acetonitrile+0.1% formic acid—flow rate 0.8 ml/min. Detection—In-line DAD set at 254 nM wavelength Method 7

CHIRALPAK 1A (250×4.6 mm, 5 µM), elution with A, 0.05% TFA in EtOH; B, heptane; D, IPA (A:B:D=40:30:30),—flow rate 0.7 ml/min. Detection—In-line DAD set at 225 nM wavelength Detection—MS, ELS, UV PDA. MS ionisation method—Electrospray (positive/negative ion)

Method 8

Waters Micromass ZQ2000 with a Acquity BEH or Acquity BEH Shield RP18 1.7 uM 100×2.1 mm C18-reverse-phase column, elution with A: water+0.1% formic acid; B: acetonitrile+0.1% formic acid. Gradient:

| Gradient - Time | flow mL/min | % A | % B |
|---|---|---|---|
| 0.00 | 0.4 | 95 | 5 |
| 0.4 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection—MS, ELS, UV PDA. MS ionisation method—Electrospray (positive/negative ion)

Method 9

Agilent 1100 series with a CHIRALPAK IA (150×4.6 mm, 5 µm), elution with A: heptane, B: ethanol+0.05% TFA—flow rate 0.5 ml/min. Detection—In-line polarimeter and UV detection set at 270 nM wavelength. Gradient:

| Gradient - Time | flow mL/min | % A | % B |
|---|---|---|---|
| 0.00 | 0.5 | 40 | 60 |
| 20.0 | 0.5 | 40 | 60 |
| 30.0 | 0.5 | 0 | 100 |
| 45.0 | 0.5 | 0 | 100 |

Method 10

Phenomenex Gemini C18-reverse-phase column (250×21.20 mm 5 µm particle size), elution with A: water+0.1% formic acid; B: methanol+0.1% formic acid. Gradient—50% A/50% B to 5% A/95% B over 15 min—flow rate 18 mL/min. Detection—In-line UV detector set at 254 nM wavelength.

Method 11

Phenomenex Luna 3 micron C18(2) 30×4.6 mm, elution with A: water+0.1% formic acid; B: acetonitrile+0.1% formic acid. Gradient:

| Gradient - Time | flow mL/min | % A | % B |
|---|---|---|---|
| 0.00 | 2.0 | 95 | 5 |
| .50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, ELS, UV (200 µl/min split to MS with in-line HP1100 DAD detection). MS ionisation method—Electrospray (positive and negative ion)

All reactions were carried out under an atmosphere of nitrogen unless specified otherwise. Racemic rosiglitazone was used as a free base and racemic pioglitazone was used as a free base or HCl salt as indicated.

Example 1

(5R)-5-{4-[2-(5-ethylpyridin-2-yl)ethoxy]benzyl}-1,3-thiazolidine-2,4-dione trifluoroacetate

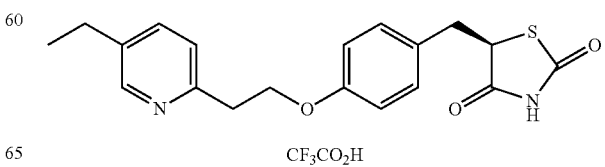

The title compound (480 mg) was isolated using method 1. LCMS (Method 4): Rt 6.00 min, m/z 357 [M-CF$_3$CO$_2$H$^+$]. [α]$_D^{25}$+104° (c 1.0, MeOH). e.e. (Method 2)≥98%, Rt 4.69 min. $^1$H NMR (400 MHz, DMSO-d$_6$): δ 12.02-11.88 (1H, bs), 8.68-8.60 (1 H, d, J 1.7), 8.32-8.23 (1 H, d, J 7.7), 7.90-7.82 (1 H, d, J 8.4), 7.14-7.06 (2 H, d, J 8.7), 6.85-6.78 (2 H, d, J 8.7), 4.85-4.78 (1 H, dd, J 4.4, 8.9), 4.35-4.27 (2 H, t, J 6.2), 3.40-3.34 (2 H, t, J 6.1), 3.28-3.21 (1 H, dd, J 4.3, 14.3), 3.05-2.97 (1 H, dd, J 9.0, 14.3), 2.77-2.67 (2 H, q, J 7.6), 1.22-1.14 (3 H, q, J 7.5).

Example 2

(5S)-5-{4-[2-(5-ethylpyridin-2-yl)ethoxy]benzyl}-1,3-thiazolidine-2,4-dione trifluoroacetate

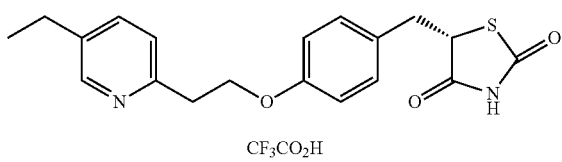 [SMILES: CCc1ccc(CCOc2ccc(C[C@@H]3SC(=O)NC3=O)cc2)nc1 ; "CF3CO2H"]

CF$_3$CO$_2$H

The title compound (674 mg) was isolated using method 1. LCMS (Method 4): Rt 6.01 min, m/z 357 [M-CF$_3$CO$_2$H$^+$]. [α]$_D^{25}$-76° (c 1.0, MeOH). e.e. (Method 2)≥98%, Rt 7.00 min. $^1$H NMR (400 MHz, DMSO-d$_6$): δ 12.02-11.88 (1H, bs), 8.68-8.60 (1 H, d, J 1.7), 8.32-8.23 (1 H, d, J 7.7), 7.90-7.82 (1 H, d, J 8.4), 7.14-7.06 (2 H, d, J 8.7), 6.85-6.78 (2 H, d, J 8.7), 4.85-4.78 (1 H, dd, J 4.4, 8.9), 4.35-4.27 (2H, t, J 6.2), 3.40-3.34 (2 H, t, J 6.1), 3.28-3.21 (1 H, dd, J 4.3, 14.3), 3.05-2.97 (1 H, dd, J 9.0, 14.3), 2.77-2.67 (2 H, q, J 7.6), 1.22-1.14 (3 H, q, J 7.5).

Example 3

(5R)-5-{4-[2-(5-ethylpyridin-2-yl)ethoxy]benzyl}-1,3-thiazolidine-2,4-dione

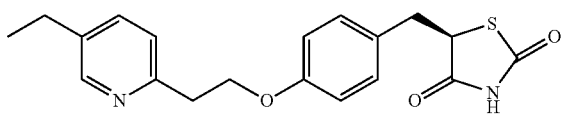 [SMILES: CCc1ccc(CCOc2ccc(C[C@H]3SC(=O)NC3=O)cc2)nc1]

MP-Carbonate (389 mg, 1.06 mmol) was added to a solution of (5R)-5-{4-[2-(5-ethylpyridin-2-yl)ethoxy]benzyl}-1,3-thiazolidine-2,4-dione trifluoroacetate (100 mg, 0.21 mmol) in MeOH (100 mL) and stirred at RT for 2 h, filtered and the resin washed with MeOH (3×10 mL). The filtrate was concentrated in vacuo to afford the title compound (35 mg, 47%). e.e. (Method 2) 92.90%, Rt 6.27 min. $^1$H NMR (400 MHz, DMSO-d$_6$): δ 12.44-11.11 (1 H, bs), 8.34-8.29 (1 H, d, J 1.9), 7.55-7.49 (1 H, dd, J 2.2, 7.9), 7.24-7.20 (1 H, d, J 7.8), 7.12-7.05 (2 H, d, J 8.6), 6.84-6.77 (2 H, d, J 8.6), 4.78-4.71 (1 H, dd, J 4.3, 9.1), 4.30-4.19 (1 H, d, J 4.3), 3.24-3.18 (2 H, d), 3.11-3.03 (2 H, t, J 6.6), 3.00-2.92 (1 H, dd, J 9.2, 14.2), 2.59-2.50 (2 H, q, J 7.6), 1.17-1.09 (3 H, t, J 7.7).

Example 4

(5R)-5-{4-[2-(5-ethylpyridin-2-yl)ethoxy]benzyl}-1,3-thiazolidine-2,4-dione hydrochloride

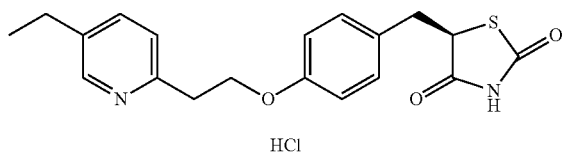 [SMILES: CCc1ccc(CCOc2ccc(C[C@H]3SC(=O)NC3=O)cc2)nc1 ; Cl]

HCl

~1.25 M HCl in MeOH (0.33 mL, 0.33 mmol) was added to a suspension of (5R)-5-{4-[2-(5-ethylpyridin-2-yl)ethoxy]benzyl}-1,3-thiazolidine-2,4-dione (from Example 1) (30 mg, 0.084 mmol) in MeOH (5 mL) and stirred at RT for 1 h. The solvent was removed in vacuo to afford the title compound (32.4 mg, 100%). LCMS (Method 4): Rt 5.95 min, m/z 357 [M-HCl$^+$]. e.e (Method 3) 93.2%, Rt 12.10 min. Stereochemistry at C-5 was assigned (R) configuration by single crystal X-ray diffraction analysis. [α]$_D^{24}$+108° (c 1.0, MeOH). $^1$H NMR (400 MHz, DMSO-d$_6$): δ 12.03-11.88 (1 H, bs), 8.68-8.62 (1 H, d, J 1.7), 8.34-8.25 (1 H, d, J 7.9), 7.91-7.83 (1 H, d, J 8.3), 7.14-7.05 (2 H, d, J 8.7), 6.86-6.77 (2 H, d, J 8.7), 4.85-4.77 (1 H, dd, J 4.3, 8.9), 4.38-4.28 (2 H, t, J 6.2), 3.42-3.36 (2 H, t, J 6.2), 3.28-3.20 (1 H, dd, J 9.0, 14.2), 3.06-2.96 (1 H, dd, J 9.0, 14.2), 2.77-2.67 (2 H, q, J 7.7), 1.23-1.15 (3H, t, J 7.7). Subsequent recrystallisations using MeOH-EtOAc or MeOH-Et$_2$O gave the title compound with an e.e. >97%.

Example 5

(5S)-5-{4-[2-(5-ethylpyridin-2-yl)ethoxy]benzyl}-1,3-thiazolidine-2,4-dione

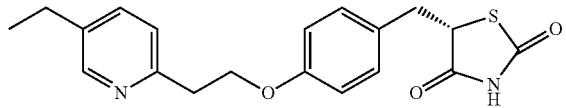 [SMILES: CCc1ccc(CCOc2ccc(C[C@@H]3SC(=O)NC3=O)cc2)nc1]

The title compound (28 mg, 37%) was prepared using a method analogous to that outlined in Example 3 starting from (5S)-5-{4-[2-(5-ethylpyridin-2-yl)ethoxy]benzyl}-1,3-thiazolidine-2,4-dione trifluoroacetate. e.e. (Method 2) 90.9%, Rt 9.21 min. $^1$H NMR (400 MHz, DMSO-d$_6$): δ 12.44-11.11 (1H, bs), 8.34-8.29 (1 H, d, J 1.9), 7.55-7.49 (1 H, dd, J 2.2, 7.9), 7.24-7.20 (1 H, d, J 7.8), 7.12-7.05 (2 H, d, J 8.6), 6.84-6.77 (2 H, d, J 8.6), 4.78-4.71 (1 H, dd, J 4.3, 9.1), 4.30-4.19 (1 H, d, J 4.3), 3.24-3.18 (2 H, d), 3.11-3.03 (2 H, t, J 6.6), 3.00-2.92 (1 H, dd, J 9.2, 14.2), 2.59-2.50 (2 H, q, J 7.6), 1.17-1.09 (3 H, t, J 7.7).

Example 6

(5S)-5-{4-[2-(5-ethylpyridin-2-yl)ethoxy]benzyl}-1,3-thiazolidine-2,4-dione hydrochloride

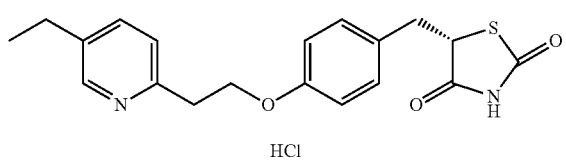 [SMILES: CCc1ccc(CCOc2ccc(C[C@@H]3SC(=O)NC3=O)cc2)nc1 ; Cl]

HCl

The title compound (25.7 mg, 100%) was prepared using a method analogous to that outlined in Example 4 starting from (5S)-5-{4-[2-(5-ethylpyridin-2-yl)ethoxy]benzyl}-1,3-thiazolidine-2,4-dione (from Example 2). LCMS (Method 4): Rt 5.94 min, m/z 357 [M-HCl$^+$]. e.e. (Method 3) 92.7%, Rt 13.25 min. Stereochemistry at C-5 was assigned (S) configuration by single crystal X-ray diffraction analysis. $[\alpha]_D^{23}$ –104° (c 1.0, MeOH). $^1$H NMR (400 MHz, DMSO-d$_6$): δ 12.03-11.88 (1 H, bs), 8.68-8.62 (1 H, d, J 1.7), 8.34-8.25 (1 H, d, J 7.9), 7.91-7.83 (1 H, d, J 8.3), 7.14-7.05 (2 H, d, J 8.7), 6.86-6.77 (2 H, d, J 8.7), 4.85-4.77 (1 H, dd, J 4.3, 8.9), 4.38-4.28 (2 H, t, J 6.0), 3.42-3.36 (2 H, t, J 6.2), 3.28-3.20 (1 H, dd, J 9.0, 14.2), 3.06-2.96 (1 H, dd, J 9.0, 14.2), 2.77-2.67 (2 H, q, J 7.7), 1.23-1.15 (3 H, t, J 7.7). Subsequent recrystallisations using MeOH-EtOAc or MeOH-Et$_2$O gave the title compound with an e.e. >97%.

Example 7

(5R)-5-(4-{2-[methyl(pyridin-2-yl)amino]ethoxy}benzyl)-1,3-thiazolidine-2,4-dione trifluoroacetate

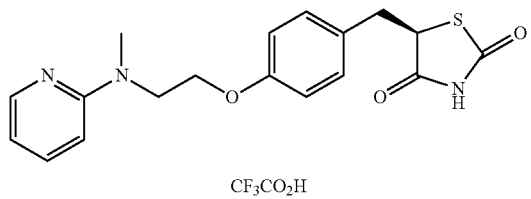

CF$_3$CO$_2$H

The title compound (149 mg) was isolated using method 5. Rt 7.14 min. $^1$H NMR (400 MHz, DMSO-d$_6$): δ 12.04-11.86 (1 H, s), 7.99-7.94 (1 H, dd, J 1.1, 6.2), 7.92-7.83 (1 H, t, J 6.6), 7.27-7.15 (1 H, d, J 8.7), 7.13-7.05 (2 H, d, J 8.6), 6.88-6.82 (1 H, t, J 6.6), 6.81-6.76 (2 H, d, J 8.7), 4.83-4.78 (1 H, dd, J 4.4, 8.8), 4.18-4.12 (2 H, t, J 5.3), 3.99-3.94 (2 H, t, J 5.3), 3.27-3.20 (1 H, dd, J 4.2, 14.4), 3.18 (3 H, s), 3.05-2.97 (1 H, dd, J 8.9, 14.6).

Example 8

(5R)-5-(4-{2-[methyl(pyridin-2-yl)amino]ethoxy}benzyl)-1,3-thiazolidine-2,4-dione hydrochloride

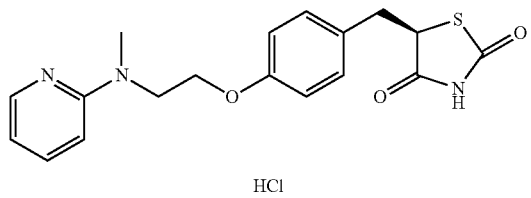 [SMILES: CN(CCOc1ccc(C[C@H]2SC(=O)NC2=O)cc1)c1ccccn1 ; Cl]

HCl

The title compound (38 mg, 64%) was prepared using method analogous to that outlined in Example 3 and 4 starting from (5R)-5-{4-[2-methyl-2-pyridylamino)ethoxy]benzyl}-1,3-thiazolidine-2,4-dione trifluoroacetate. $[\alpha]_D^{26}$ +100° (c 1.0, MeOH). LCMS (Method 4): Rt 5.41 min, m/z 358 [M-HCl$^+$]. e.e. (Method 6) 85.7%, Rt 8.03 min. $^1$H NMR (400 MHz, DMSO-d$_6$): δ 12.09-11.81 (1 H, s), 7.98-7.94 (1 H, dd, J 1.1, 6.3), 7.93-7.82 (1 H, m), 7.31-7.14 (1 H, bs), 7.13-7.05 (2 H, d, J 8.5), 6.90-6.82 (1 H, t, J 6.7), 6.80-6.76 (2 H, d, J 8.5), 4.84-4.78 (1 H, dd, J 4.4, 8.9), 4.19-4.12 (2 H, t, J 5.2), 4.02-3.94 (2 H, t, J 5.2), 3.27-3.21 (1 H, dd, J 4.4, 10.1), 3.20 (3 H, s), 3.05-2.97 (1 H, dd, J 9.0, 14.2).

R-enantiomer with greater than 90% e.e. can be obtained using literature procedures, J. Chem. Soc. Perkin Trans. 1. 1994, 3319-3324.

Example 9

(5S)-5-(4-{2-[methyl(pyridin-2-yl)amino]ethoxy}benzyl)-1,3-thiazolidine-2,4-dione hydrochloride monohydrate

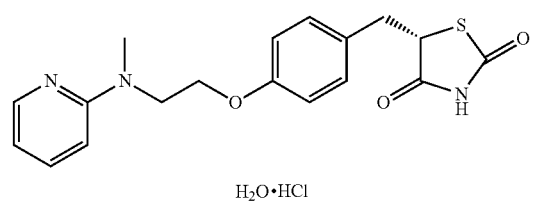 [SMILES: CN(CCOc1ccc(C[C@@H]2SC(=O)NC2=O)cc1)c1ccccn1 ; Cl ; O]

H$_2$O·HCl

The title compound (123 mg) was prepared using literature procedures, J. Chem. Soc. Perkin Trans. 1. 1994, 3319-3324. $[\alpha]_D^{23}$ –100° (c 1.0, MeOH). LCMS (Method 4): Rt 5.44 min, m/z 358 [M-HCl$^+$]. e.e. (Method 6) 92.7%, Rt 8.99 min. Stereochemistry at C-5 was assigned (S) configuration by single crystal X-ray diffraction analysis. $^1$H NMR (400 MHz, DMSO-d$_6$): δ 12.01-11.88 (1 H, s), 7.98-7.94 (1 H, dd, J 1.4, 6.1), 7.93-7.86 (1 H, t, J 7.7), 7.31-7.18 (1 H, m), 7.12-7.05 (2 H, d, J 8.7), 6.90-6.83 (1 H, t, J 6.3), 6.81-6.75 (2 H, d, J 8.7), 4.83-4.78 (1 H, dd, J 4.5, 8.8), 4.19-4.13 (2 H, t, J 5.1), 4.02-3.96 (2 H, t, J 5.1), 3.26-3.22 (1 H, m), 3.21 (3 H, s), 3.05-2.97 (1 H, dd, J 8.8, 14.0).

Example 10

(5R)-5-{4-[2-(5-ethylpyridin-2-yl)ethoxy]benzyl}-1,3-thiazolidine-2,4-dione(−)-O,O'-dibenzoyl-L-tartrate

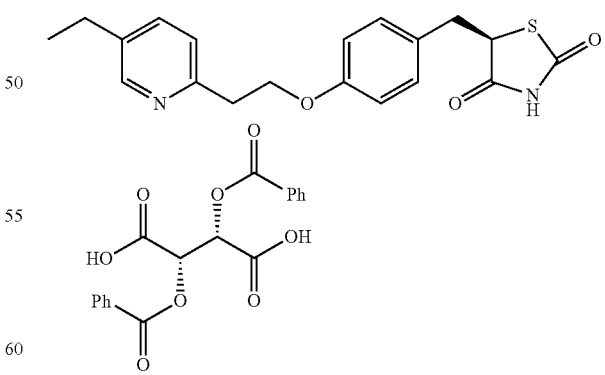

10a. To a mixture of (5R)-5-{4-[2-(5-ethylpyridin-2-yl)ethoxy]benzyl}-1,3-thiazolidine-2,4-dione hydrochloride (50 mg) (example 4) and (−)-dibenzoyl-L-tartaric acid (50 mg) was added MeOH (1.5 mL). The clear solution was rapidly stirred whilst adding H$_2$O dropwise until a cloudiness persisted. The reaction was allowed to stand at ambident temperature over 48 h and the solid collected by filtration to give the title compound (43 mg). (Method 7) 99.01% Rt 10.83 min, 0.98% Rt 15.83 min; d.e. 98.03%

10b. A slurry of (−)-dibenzoyl-L-tartaric acid (1.0 g, 2.79 mmol) in $H_2O$ (20 mL) was stirred at ambident temperature and a solution of 5-{4-[2-(5-ethylpyridin-2-yl)ethoxy]benzyl}-1,3-thiazolidine-2,4-dione hydrochloride (1.01 g, 2.57 mmol) in MeOH (20 mL) was added over 5 min. When addition was complete, the product from Example 10a (5 mg) was added and the reaction allowed to stir for 93 h. The reaction was filtered and the solid dried to give the title compound (0.863 g). (Method 7) 79.72%, Rt 10.82 min.; 20.27%, Rt 15.14 min.; d.e. 59.45%.

10c. The product from Example 10b (0.863 g) was dissolved in MeOH (8.5 mL) containing 1M HCl (1.21 mL) and $H_2O$ (5 mL) added dropwise. The product from Example 10a (1 mg) was added followed by dropwise addition of $H_2O$ (2.3 mL). The reaction was allowed to stir for 22 h, filtered, the solid washed with $H_2O$-MeOH (2:1, 3 mL) and dried at 40° C. under high vacuum to give the title compound (0.582 g). (Method 7) 93.2%, Rt 10.82 min.; 6.8%, Rt 15.14 min.; d.e. 86.4%.

10d. The product from Example 10c (0.582 g) was dissolved in MeOH (5.5 mL) containing 1M HCl (0.795 mL) and $H_2O$ (2 mL) added dropwise. The product from Example 10a (1 mg) was added followed by dropwise addition of $H_2O$ (3.5 mL). The reaction was allowed to stir for 22 h, filtered, the solid washed with $H_2O$-MeOH (2:1, 3 mL) and dried at 40° C. under high vacuum to give the title compound (0.453 g). (Method 7) 97.3%, Rt 10.65 min.; 2.7%, Rt 14.83 min.; d.e. 94.6%. $^1$H NMR (400 MHz, DMSO-$d_6$): 14.25-13.60 (bs, 1H, $D_2O$ exchangeable), 12.05-12.00 (bs, 1H, $D_2O$ exchangeable), 8.37 (d, J=2.0 Hz, 1H), 8.02 (d, J=7.6 Hz, 4H), 7.73 (t, J=7.6 Hz, 2H), 7.60 (t, J=7.6 Hz, 5H), 7.29 (d, J=8.0 Hz, 1H), 7.13 (d, J=8.8 Hz, 2H), 6.86 (d, J=8.8 Hz, 2H), 5.88 (s, 2H), 4.86 (q, J=4.4 Hz, 1H), 4.30 (t, J=6.8 Hz, 2H), 3.30 (dd, J=4.0 & 10.0 Hz, 1H), 3.13 (t, J=6.8 Hz, 2H), 3.04 (dd, J=5.2 & 9.2 Hz, 1H), 2.60 (q, J=7.6 Hz, 2H), 1.17 (t, J=7.6 Hz, 3H).

Example 11

(5R)-5-{4-[2-(5-ethylpyridin-2-yl)ethoxy]benzyl}-1,3-thiazolidine-2,4-dione hydrochloride

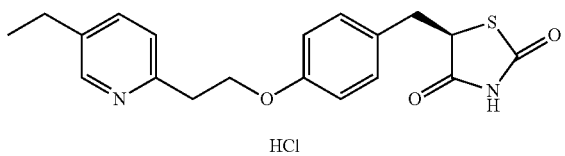 [SMILES: CCc1ccc(CCOc2ccc(C[C@H]3SC(=O)NC3=O)cc2)nc1 ; Cl]

HCl

11a. The product from Example 10d was dissolved in MeOH (2.25 mL) containing 37% HCl (0.134 mL) at 35° C. The solution was filtered, EtOAc (9 mL) was poured into the stirred solution and the mixture stirred for 20 min. The white solid was collected by filtration, washed with EtOAc and dried at 30° C. under high vacuum to give the title compound (0.181 g). (Method 7) 98.3%, Rt 10.65 min.; 1.7%, Rt 14.83 min e.e. 96.6%. LCMS (Method 8): Rt 2.90 min 99.39%, m/z 357 [MH$^+$—HCl]. LCMS (Method 11) Rt 2.91 min, m/z 357 [MH$^+$—HCl]. $^1$H NMR (400 MHz, DMSO-$d_6$): δ 12.0 (1 H, s), 8.70 (1 H, d, J 1.7 Hz), 8.36 (1 H, bd, J 8.3 Hz), 7.93 (1 H, d, J 8.2 Hz), 7.15, 6.87 (4 H, A2B2q, J 8.7 Hz), 4.86 (1 H, dd, J 4.4, 8.9 Hz), 4.38 (2 H, t, J 6.3 Hz), 3.44 (2 H, t, J 6.2 Hz), 3.29 (1 H, dd, J 4.3, 14.2 Hz), 3.06 (1 H, dd, J 9.0, 14.3 Hz), 2.78 (2H, q, J 7.6 Hz), 1.23 (3 H, t, J 7.6 Hz).

11b. The product from Example 10c (1 g) could also be reacted as described in Example 11a to give the title compound (473 mg). (Method 7) 95.6%, Rt 10.65 min.; 4.3%, Rt 14.83 min e.e.

91.3%. All other characterisation data was the same as Example 11a.

Biological Results

Example 14

Pre-Clinical Mouse Model of COPD Inflammation—Tobacco Smoke Induced Pulmonary Inflammation Previous studies have established that the number of inflammatory cells recovered in the bronchoalveolar lavage (BAL) is significantly elevated 24 h following the final Tobacco Smoke (TS) exposure of 4 or 11 consecutive daily TS exposures, this time point was used in the studies reported here.

Protocols for the exposure of mice to TS, obtaining bronchoalveolar lavage (BAL), preparation of cytospin slides for differential cell counts are as outlined below.

Exposure of Mice to TS Daily for 4 or 11 Consecutive Days

In this exposure protocol, mice were exposed in groups of 5 in individual clear polycarbonate chambers (27 cm×16 cm×12 cm). The TS from the cigarettes was allowed to enter the exposure chambers at a flow rate of 100 ml/min. In order to minimise any potential problems caused by repeated exposure to a high level of TS (6 cigarettes), the exposure of the mice to TS was increased gradually over the exposure period to a maximum of 6 cigarettes. The exposure schedule used for 4 days was as follows:

| Day 1: | 4 cigarettes | (approximately 32 min exposure) |
| Day 2: | 4 cigarettes | (approximately 32 min exposure) |
| Day 3: | 6 cigarettes | (approximately 48 min exposure) |
| Day 4: | 6 cigarettes | (approximately 48 min exposure) |

The exposure schedule used for 11 days exposure was as follows:

| Day 1: | 2 cigarettes | (approximately 16 min exposure) |
| Day 2: | 3 cigarettes | (approximately 24 min exposure) |
| Day 3: | 4 cigarettes | (approximately 32 min exposure) |
| Day 4: | 5 cigarettes | (approximately 40 min exposure) |
| Day 5 to 11: | 6 cigarettes | (approximately 48 min exposure) |

A further group of mice were exposed to air on a daily basis for equivalent lengths of time as controls (no TS exposure).

Bronchoalveolar Lavage (BAL) Analysis

Bronchoalveolar lavage was performed as follows: the trachea was cannulated using a Portex nylon intravenous cannula (pink luer fitting) shortened to approximately 8 mm. Phosphate buffered saline (PBS) was used as the lavage fluid. A volume of 0.4 ml was gently instilled and withdrawn 3 times using a 1 ml syringe and then placed in an Eppendorf tube and kept on ice prior to subsequent determinations.

Cell Counts:

Lavage fluid was separated from cells by centrifugation and the supernatant decanted and frozen for subsequent analysis. The cell pellet was re-suspended in a known volume of PBS and total cell numbers calculated by counting a stained (Turks stain) aliquot under a microscope using a haemocytometer.

Differential Cell Counts were Performed as Follows:

The residual cell pellet was diluted to approximately $10^5$ cells per ml. A volume of 500 µl was placed in the funnel of a cytospin slide and centrifuged for 8 min at 800 rpm. The slide was air dried and stained using 'Kwik-Diff' solutions (Shandon) as per the proprietary instructions. When dried and cover-slipped, differential cells were counted using light microscopy. Up to 400 cells were counted by unbiased operator using light microscopy. Cells were differentiated using standard morphometric techniques.

Drug Treatment

Rodents such as mice and rats are obligate nasal breathers thus oral delivery of test materials (such as therapeutic agents) for inhalation will not produce good lung exposure. As a consequence, delivery of therapeutic agents to the lungs in rodents is generally achieved by intra-nasal, intra-tracheal or inhalation by whole body aerosol exposure in a chamber.

The chamber method utilises large amounts of test material and is generally reserved for inhalation toxicology studies rather than pharmacological efficacy studies. Intra-tracheal administration is a very efficient delivery method as almost all of the test material is delivered to the lungs, but this is quite an invasive technique. For studies in the mouse particularly, it is also quite technically demanding as the diameter of the trachea is quite small. The intranasal route is less invasive than the intra-tracheal route and so is particularly suitable for repeat dosing studies such as the 4-11 day mouse model described below. Following intranasal administration ~50% of the dose administered is delivered to the lungs (Eyles J E, Williamson E D and Alpar H O. 1999, Int J Pharm, 189(1): 75-9).

As a surrogate route for oral inhalation, mice were dosed intra-nasally with vehicle (0.2% tween 80 in saline), 5S-pioglitazone (as prepared in Example 6) (3 µg/kg), 5S-pioglitazone (as prepared in Example 6) (1 µg/kg), 5R-pioglitazone (as prepared in Example 4) (3 µg/kg), 5R-pioglitazone (as prepared in Example 4) (1 µg/kg), or racemic pioglitazone (3 µg/kg). The control group of mice received vehicle 1 hr prior to being exposed to air daily for a maximum of 50 minutes per day. BAL was performed 24 h following the final TS exposure. All compounds were dosed as the HCl salt with doses corrected as base.

In a second experiment, mice were dosed intra-nasally with vehicle (0.2% tween 80 in saline), 5S-Rosiglitazone (as prepared in Example 9) (3 µg/kg), 5S-Rosiglitazone (as prepared in Example 9) (10 µg/kg), 5R-Rosiglitazone (as prepared in Example 8) (3 µg/kg), 5R-Rosiglitazone (as prepared in Example 8) (10 µg/kg), or racemic Rosiglitazone (10 µg/kg). The control group of mice received vehicle 1 hr prior to being exposed to air daily for a maximum of 50 minutes per day. BAL was performed 24 h following the final TS exposure. All compounds were dosed as the HCl salt with doses corrected as free base.

Data Management and Statistical Analysis

All results are presented as individual data points for each animal and the mean value was calculated for each group. Since tests for normality were positive, the data were subjected to a one way analysis of variance test (ANOVA), followed by a Bonferroni correction for multiple comparisons in order to test for significance between treatment groups. A "p" value of <0.05 was considered to be statistically significant. Percentage inhibitions were automatically calculated within the Excel spreadsheets for the cell data using the formula below:

$$\% \text{ Inhibition} = 1 - \left(\frac{\text{Treatment group result} - \text{sham group result}}{TS \text{ vehicle group result} - \text{sham group result}}\right) \times 100$$

Inhibition data for other parameters were calculated manually using the above formula.

As illustrated in FIG. 1, there was a clear difference in activity between the two enantiomers of pioglitazone on total cell BAL numbers following exposure to TS. The 5R enantiomer (e.e. 97.8%) of Pioglitazone significantly inhibited the BAL cell influx induced by TS at both 1 and 3 µg/kg when administered by the intranasal route. In contrast, the 5S-enantiomer (e.e. 97.5%) failed to inhibit the BAL cell inflammation at either dose examined.

Figure 2:
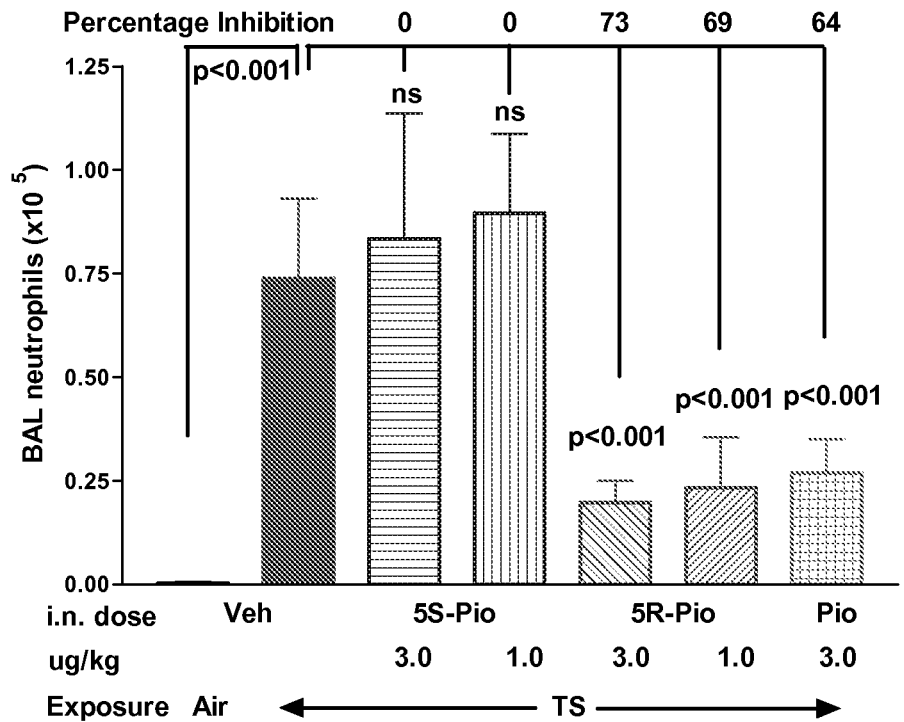
FIG. 2 is a bar graph that illustrates the effect of intranasal administration to laboratory mice with vehicle (0.2% tween 80 in saline), 5S-pioglitazone (1 or 3 µg/kg), 5R-pioglitazone (1 or 3 µg/kg), or racemic pioglitazone (3 µg/kg) on the number of BAL neutrophils induced by tobacco smoke 24 hours post the final exposure.

Following examination of the BAL cell cytospins, BAL neutrophil numbers were determined. In concert with the activity on total BAL cells, the 5R enantiomer of pioglitazone significantly inhibited BAL neutrophil numbers induced by TS exposure at both doses whereas the 5S enantiomer of pioglitazone was ineffective (FIG. 2).

Racemic pioglitazone (which contains 50% 5R enantiomer of pioglitazone) at the 3 µg/kg dose also significantly inhibited total and neutrophil BAL cells induced by TS.

Figure 3:
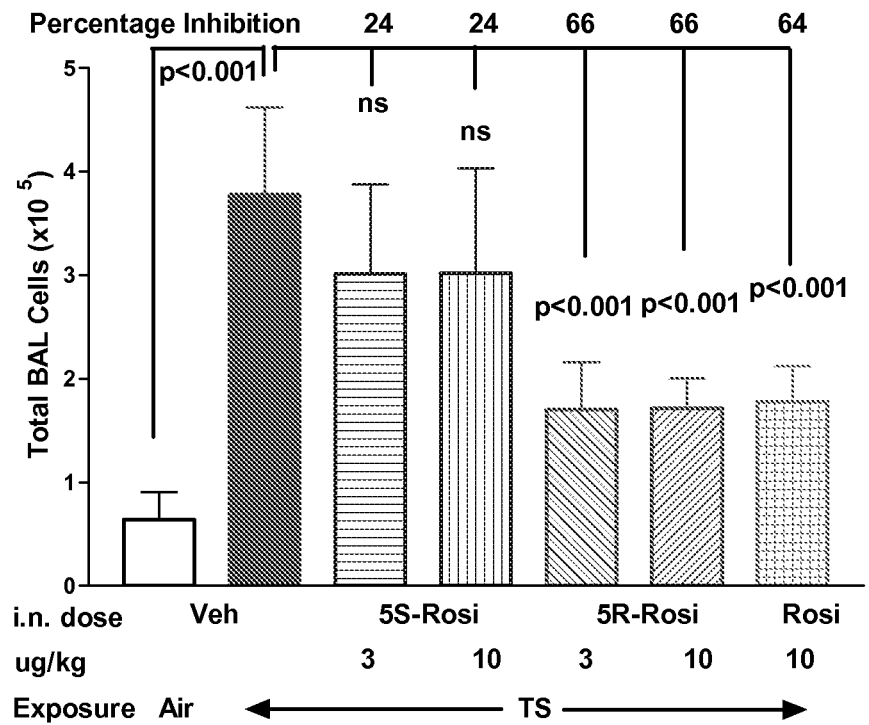
FIG. 3 is a bar graph that illustrates the effect of intranasal administration to laboratory mice with vehicle (0.2% tween 80 in saline), 5S-Rosiglitazone (3 or 10 µg/kg), 5R-Rosiglitazone (3 or 10 µg/kg), or racemic Rosiglitazone (10 µg/kg) on the number of BAL cells induced by tobacco smoke 24 hours post the final exposure.
Figure 4:
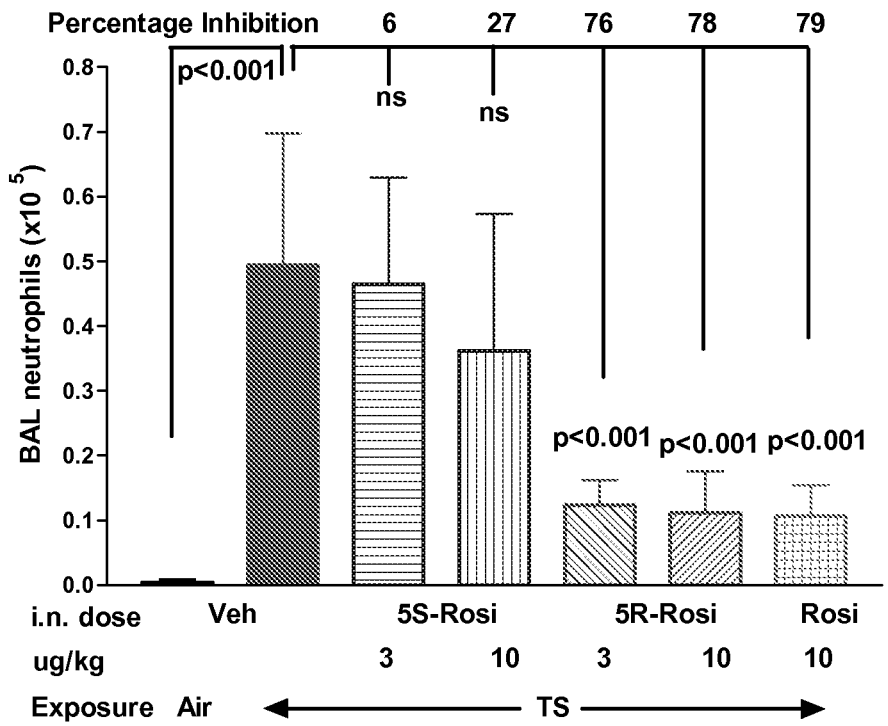
FIG. 4 is a bar graph that illustrates the effect of intranasal administration to laboratory mice with vehicle (0.2% tween 80 in saline), 5S-Rosiglitazone (3 or 10 µg/kg), 5R-Rosiglitazone (3 or 10 µg/kg), or racemic Rosiglitazone (10 µg/kg) on the number of BAL neutrophils induced by tobacco smoke 24 hours post the final exposure.

As illustrated in FIG. 3, there was a clear difference in activity between the two enantiomers of Rosiglitazone on total cell BAL numbers following exposure to TS. The 5R enantiomer (e.e. 85.7%) of Rosiglitazone significantly inhibited the BAL cell influx induced by TS at both 3 and 10 µg/kg when administered by the intranasal route. In contrast, the 5S-enantiomer (e.e. 92.7%) failed to inhibit the BAL cell inflammation at either dose examined.

Following examination of the BAL cell cytospins, BAL neutrophil numbers were determined. In concert with the activity on total BAL cells, the 5R enantiomer of Rosiglitazone significantly inhibited BAL neutrophil numbers induced by TS exposure at both doses whereas the 5S enantiomer of Rosiglitazone was ineffective (FIG. 2).

Racemic rosiglitazone (which contains 50% 5R enantiomer of Rosiglitazone) at the 10 µg/kg dose also significantly inhibited total and neutrophil BAL cells induced by TS.

Taken together, the results of the two studies identify the 5R enantiomer of both Pioglitazone and Rosiglitazone as possessing the anti-inflammatory activity required for inhibition of BAL cell influx whilst the 5S enantiomer does not.

Whilst the e.e. of the preparation of the 5R enantiomer of Rosiglitazone was lower than optimal (i.e., 85.7% rather than >90%) differential activity of the two enantiomers was still observed. This suggests that an optimal preparation of 5R enantiomer of Rosiglitazone would show similar or even improved activity compared with the data presented herein. Therefore the data presented herein is indicative of what would be achieved with a preparation that contains by weight at least 95% 5R enantiomer of Rosiglitazone.

Process Development Examples

In the following description of process development work, the Preliminary Example describes the preparation of seed crystals of 5R-pioglitazone O,O'-dibenzoyl-L-tartrate for use in the method of the invention, and of seed crystals of 5R-pioglitazone hydrochloride; Examples 15-20 describe methods according to the invention; and Comparative Examples 1-18 describe potential alternative resolution methods and conditions which were unsatisfactory for the large scale resolution of racemic pioglitazone.

Abbreviations used in the process development examples: c=concentration; h=hour; $H_2O$=distilled water; HPLC=high performance liquid chromatography;

LCMS=liquid chromatography mass spectrometry; MeOH=methanol; TFA=trifluoroacetic acid; DMSO=dimethyl sulphoxide; HCl=hydrogen chloride; EtOH=ethanol; IPA=isopropyl alcohol; EtOAc=ethyl acetate; THF=tetrahydrofuran; NH$_4$Cl=ammonium chloride; LDA=lithium diisopropylamide; CHCl$_3$=chloroform; CH$_3$CN=acetonitrile; min=minutes; RT=room temperature; Rt=retention time; e.e.=enantiomeric excess; d.e.=diastereomeric excess; SL-W003-2=(S)-1-[(S)-2-(2i-diphenylphosphinophenyl)ferrocenyl]ethyldicyclohexyl phosphine; pioglitazone=5-{4-[2-(5-ethylpyridin-2-yl)ethoxy]benzyl}-1,3-thiazolidine-2,4-dione; L-DBTA=L-dibenzoyl tartaric acid; Rh(COD)$_2$BF$_4$=bis(1,5-cyclooctadiene) Rhodium I tetrafluoroborate; MP-Carbonate=macroporous triethylammonium methylpolystyrene carbonate (0.5% inorganic antistatic agent); (±)5-{4-[2-(5-ethylpyridin-2-yl)ethoxy]benzyl}-1,3-thiazolidine-2,4-dione hydrochloride=(±)Pioglitazone hydrochloride; (5R) 5-{4-[2-(5-ethylpyridin-2-yl)ethoxy]benzyl}-1,3-thiazolidine-2,4-dione hydrochloride=(5R)Pioglitazone hydrochloride; 5-{4-[2-(5-ethylpyridin-2-yl)ethoxy]benzyl}-1,3-thiazolidine-2,4-dione(−)-O,O'-dibenzoyl-L-tartrate=(5R)Pioglitazone.L-DBTA.

The nomenclature of structures was assigned using ACD Labs version 10.

NMR spectra were obtained on a Varian Unity Inova 400 spectrometer with a 5 mm inverse detection triple resonance probe operating at 400 MHz or on a Bruker Avance DRX 400 spectrometer with a 5 mm inverse detection triple resonance TXI probe operating at 400 MHz or on a Bruker Avance DPX 300 spectrometer with a standard 5 mm dual frequency probe operating at 300 MHz or a Varian Mercury Plus operating at 400 MHz. Shifts are given in ppm relative to tetramethylsilane. Optical rotations were measured using an AA-10R automatic polarimeter with 5×25 mm jacketed sample cell or a Jasco-P-2000 polarimeter. Asymmetric hydrogenolysis experiments were performed using Biotage Endeavor hydrogenation equipment. Infrared spectra were recorded using a Shimadzu IR Prestage-21 instrument. Mass spectra were recorded using an Applied Biosystems API3000 LC/MS/MS.

All solvents and commercial reagents were used as received.

The Liquid Chromatography Mass Spectroscopy (LC/MS) and HPLC systems used:

Method 1

CHIRALPAK 1A (250×4.6 mm, 5 μM), elution with A, 0.05% TFA in EtOH; B, heptane; D, IPA (A:B:D=40:30:30),—flow rate 0.7 ml/min. Detection—In-line DAD set at 225 nM wavelength. Detection—MS, ELS, UV PDA. MS ionisation method—Electrospray (positive/negative ion).

Method 2

Waters Micromass ZQ2000 with a Acquity BEH or Acquity BEH Shield RP18 1.7 uM 100×2.1 mm C18-reverse-phase column, elution with A: H$_2$O+0.1% formic acid; B: CH$_3$CN+0.1% formic acid. Gradient:

| Gradient - Time | flow mL/min | % A | % B |
|---|---|---|---|
| 0.00 | 0.4 | 95 | 5 |
| 0.4 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection—MS, ELS, UV PDA. MS ionisation method—Electrospray (positive/negative ion)

Method 3

Phenomenex Luna 3 micron C18(2) 30×4.6 mm, elution with A: H$_2$O+0.1% formic acid; B: CH$_3$CN+0.1% formic acid. Gradient:

| Gradient - Time | flow mL/min | % A | % B |
|---|---|---|---|
| 0.00 | 2.0 | 95 | 5 |
| .50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, ELS, UV (200 μl/min split to MS with in-line HP1100 DAD detection). MS ionisation method—Electrospray (positive and negative ion)

Method 4

Agilent 1100 series with a CHIRALPAK IA (150×4.6 mm, 5 μm), elution with A: heptane, B: ethanol+0.05% TFA—flow rate 0.5 ml/min. Detection—In-line polarimeter and UV detection set at 270 nM wavelength.

Gradient:

| Gradient - Time | flow mL/min | % A | % B |
|---|---|---|---|
| 0.00 | 0.5 | 40 | 60 |
| 20.0 | 0.5 | 40 | 60 |
| 30.0 | 0.5 | 0 | 100 |
| 45.0 | 0.5 | 0 | 100 |

Method 5

Phenomenex Gemini C18-reverse-phase column (250×21.20 mm 5 μm particle size), elution with A: H$_2$O+0.1% formic acid; B: methanol+0.1% formic acid. Gradient—50% A/50% B to 5% A/95% B over 15 min—flow rate 18 mL/min. Detection—In-line UV detector set at 254 nM wavelength.

Method 6

CHIRALPAK 1A (250×4.6 mm, 5 μM), elution with ethanol+0.05% TFA—flow rate 0.7 ml/min. Detection—In-line DAD set at 225 nM wavelength Method 7

CHIRALPAK IA (250 mm×4.6 mm 5 μm), A, 0.05% TFA in EtOH; B, hexane; D, IPA (A:B:D=40:30:30),—flow rate 0.7 ml/min. Detection—In-line DAD set at 225 nM wavelength Method 8

ACE5 C18 (250 mm×4.0 mm, 5 μm) elution with A, 0.01 M KH$_2$PO$_4$ (pH 3.0); B, ACN; RT 5.82 min. Detection by UV wavelength at 222 nm. Flow rate 0.7 ml/min.

Method 9

CHIRALPAK AD-H (250×30 mm, 5 μm), elution with EtOH+0.05% TFA—flow rate 30 ml/min. Detection—In-line UV detection set at 250 nM wavelength Method 10

CHIRALPAK 1A (250×4.6 mm, 5 μM), elution with EtOH+0.05% TFA—flow rate 0.7 ml/min. Detection—In-line DAD set at 280 nM wavelength Method 11

CHIRALCEL OD-RH (150×4.6 mm), elution with 90% MeOH+10% H$_2$O—flow rate 0.5 ml/min. Detection—In-line UV detection set at 254 nM wavelength Method 12

Waters Micromass ZQ2000 with a C18-reverse-phase column (100×3.0 mm Higgins Clipeus with 5 μm particle size), elution with A: water+0.1% formic acid; B: acetonitrile+0.1% formic acid. Gradient:

| Gradient - Time | flow mL/min | % A | % B |
| --- | --- | --- | --- |
| 0.00 | 1.0 | 95 | 5 |
| 1.00 | 1.0 | 95 | 5 |
| 15.00 | 1.0 | 5 | 95 |
| 20.00 | 1.0 | 5 | 95 |
| 22.00 | 1.0 | 95 | 5 |
| 25.00 | 1.0 | 95 | 5 |

Detection—MS, ELS, UV (100 μl split to MS with in-line UV detector). MS ionisation method—Electrospray (positive ion)

Method 13

CHIRALPAK IA (250 mm×4.6 mm 5 μm), A, 0.05% TFA in EtOH; B, hexane; D, IPA (A:B:D=40:30:30),—flow rate 0.7 ml/min. Detection—In-line DAD set at 280 nM wavelength Method 14

CHIRALCEL OJ-RH (150×4.6 mm), elution with 90% MeOH+10% $H_2O$—flow rate 0.5 ml/min. Detection—In-line UV detection set at 254 nM wavelength All reactions were carried out under an atmosphere of nitrogen unless specified otherwise. Racemic pioglitazone was used as a free base or HCl salt as indicated.

Preliminary Example (Seed Crystal Preparations)

Step a. (5R)-5-{4-[2-(5-ethylpyridin-2-yl)ethoxy]benzyl}-1,3-thiazolidine-2,4-dione trifluoroacetate The title compound (480 mg) was isolated from racemic 5-{4-[2-(5-ethylpyridin-2-yl)ethoxy]benzyl}-1,3-thiazolidine-2,4-dione by chiral chromatography using method 9. LCMS (Method 12): Rt 6.00 min, m/z 357 [M-$CF_3CO_2H^+$]. $[\alpha]_D^{25}$+104° (c 1.0, MeOH). e.e. (Method 10) ≥98%, Rt 4.69 min. $^1$H NMR (400 MHz, DMSO-$d_6$): δ 12.02-11.88 (1H, bs), 8.68-8.60 (1 H, d, J 1.7), 8.32-8.23 (1 H, d, J 7.7), 7.90-7.82 (1 H, d, J 8.4), 7.14-7.06 (2 H, d, J 8.7), 6.85-6.78 (2 H, d, J 8.7), 4.85-4.78 (1 H, dd, J 4.4, 8.9), 4.35-4.27 (2 H, t, J 6.2), 3.40-3.34 (2 H, t, J 6.1), 3.28-3.21 (1 H, dd, J 4.3, 14.3), 3.05-2.97 (1 H, dd, J 9.0, 14.3), 2.77-2.67 (2 H, q, J 7.6), 1.22-1.14 (3 H, q, J 7.5).

Step b. (5R)-5-{4-[2-(5-ethylpyridin-2-yl)ethoxy]benzyl}-1,3-thiazolidine-2,4-dione MP-Carbonate (389 mg, 1.06 mmol) was added to a solution of (5R)-5-{4-[2-(5-ethylpyridin-2-yl)ethoxy]benzyl}-1,3-thiazolidine-2,4-dione trifluoroacetate (100 mg, 0.21 mmol) in MeOH (100 mL) and stirred at RT for 2 h. The reaction was decanted to leave the resin which was washed with MeOH (3×10 mL) and the combined MeOH fractions were removed in vacuo to afford the title compound (35 mg, 47%). e.e. (Method 10) 92.90%, Rt 6.27 min. $^1$H NMR (400 MHz, DMSO-$d_6$): δ 12.44-11.11 (1 H, bs), 8.34-8.29 (1 H, d, J 1.9), 7.55-7.49 (1 H, dd, J 2.2, 7.9), 7.24-7.20 (1H, d, J 7.8), 7.12-7.05 (2 H, d, J 8.6), 6.84-6.77 (2 H, d, J 8.6), 4.78-4.71 (1 H, dd, J 4.3, 9.1), 4.30-4.19 (1 H, d, J 4.3), 3.24-3.18 (2 H, d), 3.11-3.03 (2 H, t, J 6.6), 3.00-2.92 (1 H, dd, J 9.2, 14.2), 2.59-2.50 (2 H, q, J 7.6), 1.17-1.09 (3 H, t, J 7.7).

Step c. (5R)-5-{4-[2-(5-ethylpyridin-2-yl)ethoxy]benzyl}-1,3-thiazolidine-2,4-dione hydrochloride seed crystals ~1.25 M HCl in MeOH (0.33 mL, 0.33 mmol) was added to a suspension of (5R)-5-{4-[2-(5-ethylpyridin-2-yl)ethoxy]benzyl}-1,3-thiazolidine-2,4-dione (30 mg, 0.084 mmol) in MeOH (5 mL) and stirred at RT for 1 h. The solvent was removed in vacuo to afford the title compound (32.4 mg, 100%). LCMS (Method 12): Rt 5.95 min, m/z 357 e.e (Method 11) 93.2%, Rt 12.10 min. Stereochemistry at C-5 was assigned (R) configuration by single crystal X-ray diffraction analysis. $[\alpha]_D^{24}$+108° (c 1.0, MeOH). $^1$H NMR (400 MHz, DMSO-$d_6$): δ 12.03-11.88 (1 H, bs), 8.68-8.62 (1 H, d, J 1.7), 8.34-8.25 (1 H, d, J 7.9), 7.91-7.83 (1 H, d, J 8.3), 7.14-7.05 (2 H, d, J 8.7), 6.86-6.77 (2 H, d, J 8.7), 4.85-4.77 (1 H, dd, J 4.3, 8.9), 4.38-4.28 (2 H, t, J 6.0), 3.42-3.36 (2 H, t, J 6.2), 3.28-3.20 (1 H, dd, J 9.0, 14.2), 3.06-2.96 (1 H, dd, J 9.0, 14.2), 2.77-2.67 (2 H, q, J 7.7), 1.23-1.15 (3 H, t, J 7.7). Subsequent recrystallisations using MeOH-EtOAc or MeOH-$Et_2O$ gave the title compound with an e.e. >97%.

Step d. (5R)-5-{4-[2-(5-ethylpyridin-2-yl)ethoxy]benzyl}-1,3-thiazolidine-2,4-dione(−)-O,O'-dibenzoyl-L-tartrate seed crystals To a mixture of (5R)-5-{4-[2-(5-ethylpyridin-2-yl)ethoxy]benzyl}-1,3-thiazolidine-2,4-dione hydrochloride (50 mg) (preliminary example, step c) and L-DBTA (50 mg) was added MeOH (1.5 mL). The clear solution was rapidly stirred whilst adding $H_2O$ dropwise until a cloudiness persisted. The reaction was allowed to stand at ambident temperature over 48 h and the solid collected by filtration to give the title compound (43 mg). (Method 1) 99.01% Rt 10.83 min, 0.98% Rt 15.83 min; d.e. 98.03%. $^1$H NMR (400 MHz, DMSO-$d_6$): 14.25-13.60 (bs, 1 H, $D_2O$ exchangeable), 12.05-12.00 (bs, 1 H, $D_2O$ exchangeable), 8.37 (d, J=2.0 Hz, 1H), 8.02 (d, J=7.6 Hz, 4H), 7.73 (t, J=7.6 Hz, 2H), 7.60 (t, J=7.6 Hz, 5H), 7.29 (d, J=8.0 Hz, 1H), 7.13 (d, J=8.8 Hz, 2H), 6.86 (d, J=8.8 Hz, 2H), 5.88 (s, 2H), 4.86 (q, J=4.4 Hz, 1H), 4.30 (t, J=6.8 Hz, 2H), 3.30 (dd, J=4.0 & 10.0 Hz, 1H), 3.13 (t, J=6.8 Hz, 2H), 3.04 (dd, J=5.2 & 9.2 Hz, 1H), 2.60 (q, J=7.6 Hz, 2H), 1.17 (t, J=7.6 Hz, 3H).

Example 15

(5R)-5-{4-[2-(5-ethylpyridin-2-yl)ethoxy]benzyl}-1,3-thiazolidine-2,4-dione(−)-O,O'-dibenzoyl-L-tartrate (Small Scale)

Step 1. A slurry of L-DBTA (1.0 g, 2.79 mmol) in $H_2O$ (20 mL) was stirred at ambident temperature and a solution of racemic 5-{4-[2-(5-ethylpyridin-2-yl)ethoxy]benzyl}-1,3-thiazolidine-2,4-dione hydrochloride (1.01 g, 2.57 mmol) in MeOH (20 mL) was added over 5 min. When addition was complete, seed crystals from Preliminary Example (5 mg) was added and the reaction allowed to stir for 93 h. The reaction was filtered and the solid dried to give the title compound (0.863 g). (Method 1) 79.72%, Rt 10.82 min.; 20.27%, Rt 15.14 min.; d.e. 59.45%.

Step 2. The product from Step 1 (0.863 g) was dissolved in MeOH (8.5 mL) containing 1M HCl (1.21 mL) and $H_2O$ (5 mL) added dropwise. Seed crystals from Preliminary Example Step d (1 mg) were added followed by dropwise addition of $H_2O$ (2.3 mL). The reaction was allowed to stir for 22 h, filtered, the solid washed with $H_2O$-MeOH (2:1, 3 mL) and dried at 40° C. under high vacuum to give the title compound (0.582 g), d.e. 86.4%.

Step 3. The product from Step 2 (0.582 g) was dissolved in MeOH (5.5 mL) containing 1M HCl (0.795 mL) and $H_2O$ (2 mL) added dropwise. Seed crystals from Preliminary Example Step d (1 mg) were added followed by dropwise addition of $H_2O$ (3.5 mL). The reaction was allowed to stir for 22 h, filtered, the solid washed with $H_2O$-MeOH (2:1, 3 mL) and dried at 40° C. under high vacuum to give the title compound (0.453 g). (Method 1) 97.3%, Rt 10.65 min.; 2.7%, Rt 14.83 min.; d.e. 94.6%. $^1$H NMR (400 MHz, DMSO-$d_6$): 14.25-13.60 (bs, 1H, $D_2O$ exchangeable), 12.05-12.00 (bs, 1H, $D_2O$ exchangeable), 8.37 (d, J=2.0 Hz, 1H), 8.02 (d, J=7.6 Hz, 4H), 7.73 (t, J=7.6 Hz, 2H), 7.60 (t, J=7.6 Hz, 5H), 7.29 (d, J=8.0 Hz, 1H), 7.13 (d, J=8.8 Hz, 2H), 6.86 (d, J=8.8 Hz, 2H), 5.88 (s, 2H), 4.86 (q, J=4.4 Hz, 1H), 4.30 (t, J=6.8

Hz, 2H), 3.30 (dd, J=4.0 & 10.0 Hz, 1H), 3.13 (t, J=6.8 Hz, 2H), 3.04 (dd, J=5.2 & 9.2 Hz, 1H), 2.60 (q, J=7.6 Hz, 2H), 1.17 (t, J=7.6 Hz, 3H).

Example 16

(5R)-5-{4-[2-(5-ethylpyridin-2-yl)ethoxy]benzyl}-1, 3-thiazolidine-2,4-dione hydrochloride (small scale)

The product from Example 15, Step 3 was dissolved in MeOH (2.25 mL) containing 37% HCl (0.134 mL) at 35° C. The solution was filtered, EtOAc (9 mL) was poured into the stirred solution and the mixture stirred for 20 min. The white solid was collected by filtration, washed with EtOAc and dried at 30° C. under high vacuum to give the title compound (0.181 g). (Method 1) 98.3%, Rt 10.65 min.; 1.7%, Rt 14.83 min e.e. 96.6%. LCMS (Method 2): Rt 2.90 min 99.39%, m/z 357 [MH$^+$—HCl]. LCMS (Method 3) Rt 2.91 min, m/z 357 [MH$^+$—HCl]. $^1$H NMR (400 MHz, DMSO-d$_6$): δ 12.0 (1 H, s), 8.70 (1 H, d, J 1.7 Hz), 8.36 (1 H, bd, J 8.3 Hz), 7.93 (1 H, d, J 8.2 Hz), 7.15, 6.87 (4 H, A2B2q, J 8.7 Hz), 4.86 (1 H, dd, J 4.4, 8.9 Hz), 4.38 (2 H, t, J 6.3 Hz), 3.44 (2 H, t, J 6.2 Hz), 3.29 (1 H, dd, J 4.3, 14.2 Hz), 3.06 (1 H, dd, J 9.0, 14.3 Hz), 2.78 (2 H, q, J 7.6 Hz), 1.23 (3 H, t, J 7.6 Hz).

Example 17

(5R)-5-{4-[2-(5-ethylpyridin-2-yl)ethoxy]benzyl}-1, 3-thiazolidine-2,4-dione(−)-O,O'-dibenzoyl-L-tartrate (Large Scale, Two Step modification)

Step 1 of Example 15 can be carried out on a larger scale under conditions which yield the DBTA salt with a purity of greater than the 59.45% achieved in Example 15 step 1. Factors which can improve the d.e. include slow addition of water to the initial water/methanol starting mix, so that that the final volume ratio of water to methanol is in the range 0.8:1 to 1.2:1, and using a ratio of L-DBTA:pioglitazone HCL in the range 0.5:1 to 1:1, preferably the lower end of that range. The following protocol is one which results in such improvement in d.e. Table A which follows that protocol records the d.e.'s achieved by further repetitions using slightly different conditions.

To (−)-Dibenzoyl-L-tartaric acid (577.5 g, 1.61 mol) and 5-{4-[2-(5-ethylpyridin-2-yl)ethoxy]benzyl}-1,3-thiazolidine-2,4-dione hydrochloride (1.05 Kg, 2.68 mol) in MeOH (6.636 L) was added H$_2$O (2.5 L) and the mixture stirred until a solution was obtained. H$_2$O (1.896 L) was added in a steady flow into the vortex of the stirred reaction followed by (5R)-5-{4-[2-(5-ethylpyridin-2-yl)ethoxy]benzyl}-1,3-thiazolidine-2,4-dione(−)-O,O'-dibenzoyl-L-tartrate (Example 15a, 300 mg). Further H$_2$O (3.5 L) was added dropwise over 20 h using an HPLC pump. The suspension was stirred for a total of 44 h before the granular solid was collected by filtration, washed with 330 mL of premixed H$_2$O/MeOH (2:1) and dried at 40° C. under vacuum to give the title compound (917.45 g, 48%). (Method 1) 83.23%, Rt 10.17 min.; 16.76%, Rt 14.56 min.; 64.47% d.e.

TABLE A

| Part 1 | | | |
|---|---|---|---|
| | Repetition 1 | Repetition 2 | Repetition 3 |
| Pioglitazone•HCl | 1.05 kg | 1.05 kg | 1.05 kg |
| L-DBTA | 577.5 g (0.6eq) | 577.5 g (0.6eq) | 577.5 g (0.6eq) |
| MeOH | 6.636 L | 6.636 L | 6.636 L |
| H$_2$O | 7.896 L | 7.896 L | 7.396 L |
| Reaction time (h) | 42 h | ~44 h | 44 h |
| Weight, yield (%) | 917.45 g, (48%) | 952.4 g, (49.8%) | 919.29 g, (48%) |
| d.e. of DBTA salt | 64.5% | 60.4% | 70.55% |
| Part 2 | | | |
| | Repetition 4 | Repetition 5 | Repetition 6 |
| Pioglitazone•HCl | 1.05 kg | 1.05 kg | 1.05 kg |
| L-DBTA | 577.5 g (0.6eq) | 577.5 g (0.6eq) | 577.5 g (0.6eq) |
| MeOH | 6.636 L | 6.636 L | 6.636 L |
| H$_2$O | 7.111 L | 7.216 L | 7.186 L |
| Reaction time (h) | 43.5 h | 42 h | 96 h |
| Weight, yield (%) | 870.39 g, (45.5%) | 892 g, (46.6%) | 880.2 g, (46.0%) |
| d.e. of DBTA salt | 69.4% | 66.0% | 72.5% |
| Part 3 | | | |
| | Repetition 7 | Repetition 8 | |
| Pioglitazone•HCl | 1.05 kg | 1.05 kg | |
| L-DBTA | 577.5 g (0.6eq) | 577.5 g (0.6eq) | |
| MeOH | 6.636 L | 6.636 L | |
| H$_2$O | 6.53 L | 7.196 L | |
| Reaction time (h) | 96 h | 45 h | |
| Weight, yield (%) | 849.8 g, (44.4%) | 859.1 g, (44.9%) | |
| d.e. of DBTA salt | 70.5% | 64.47% | |

Step 2:

Step 2 of Example 15 can be carried out on a larger scale using the higher d.e. precipitate recoverable using the improved conditions illustrated by the protocol of Step 1 of this Example 17 and the Table A repetitions. The following protocol is one which results in a product with the desired 90% or higher d.e, thus avoiding the need for the final step 3 of Example 15. Table B which follows that protocol records the d.e.'s achieved by further repetitions using slightly different conditions.

(5R)-5-{4-[2-(5-Ethylpyridin-2-yl)ethoxy]benzyl}-1,3-thiazolidine-2,4-dione(−)-O,O'-dibenzoyl-L-tartrate (1380.4 g) (d.e 63.4%) was added to premixed MeOH (6.62 L) and 1M HCl (1.93 L). The solution was warmed to 30° C. and filtered to remove some undissolved starting material. The clear solution was stirred and water (1 L) was added over 1 min. into the vortex of the reaction. (5R)-5-{4-[2-(5-Ethylpyridin-2-yl)ethoxy]benzyl}-1,3-thiazolidine-2,4-dione(−)-O,O'-dibenzoyl-L-tartrate seed crystals (from Preliminary Example Step d) (300 mg) were added followed by dropwise addition of further H$_2$O (2.5 L) over 14 h at 3 ml/min using an HPLC pump. The slurry was stirred for 44 h then the solid was collected by filtration, washed with 330 mL premixed H$_2$O/MeOH (2:1) and dried at 40° C. under vacuum to give the title compound (976.55 g, 71%). (Method 1) 96.69%, Rt 10.48 min.; 3.30%, Rt 16.73 min.; 93.39% d.e

TABLE B

| | Repetition 2 | Repetition 3 |
|---|---|---|
| Weight Pioglitazone•LDBTA | 2.80 kg | 2.80 kg |
| Starting d.e. | 65.4% | 67.7% |
| MeOH | 6.62 L | 6.62 L |
| 1M HCl | 1.93 L | 1.93 L |
| Water | 3.3 L | 3.25 L |
| Reaction time | 68 h | 44 h |
| Weight, yield (%) | 845.08 g, (60%) | 822.5 g (58.4%) |
| Product d.e. | 92.62% | 92.4% |

TABLE B-continued

|  | Repetiton 4 | Repetition 5 |
| --- | --- | --- |
| Weight Pio•LDBTA | 2.99 kg | 2.90 kg |
| Starting d.e. | 70.1% | 66.2% |
| MeOH | 7.48 L | 6.9 L |
| 1M HCl | 2.1 L | 2.03 L |
| Water | 4.18 L | 3.97 L |
| Reaction time | 70 h | 44 h |
| Weight, yield (%) | 1109.2 g, (74%) | 952.1 g, (65.6%) |
| Product d.e. | 90.3% | 91.7% |

Example 18

(5R)-5-{4-[2-(5-ethylpyridin-2-yl)ethoxy]benzyl}-1,3-thiazolidine-2,4-dione hydrochloride (large Scale)

(5R)-5-{4-[2-(5-ethylpyridin-2-yl)ethoxy]benzyl}-1,3-thiazolidine-2,4-dione(−)-O,O'-dibenzoyl-L-tartrate d.e. 93.39% (from Example 3) (976.55 g, 1.366 mol) was split into 2 batches and dissolved in premixed MeOH (2.5 L) and concentrated HCl (148 mL) at 40-45° C. (internal temperature). The reaction was allowed to stir over <5 min to give a clear solution and was then filtered quickly through a glass fibre filter paper into a 20 L flange top reactor flask containing seed crystals of (5R)-5-{4-[2-(5-ethylpyridin-2-yl)ethoxy]benzyl}-1,3-thiazolidine-2,4-dione hydrochloride (from Preliminary Example step c) (300 mg, e.e. 94.66%). The procedure was repeated with the other Pioglitazone.L-DBTA batch. EtOAc (7.5 L) was added to the flange top reactor and the mixture was set to stir mechanically. The remaining 2.5 L EtOAc was added in a steady stream into the vortex and stirring continued over 3 h. The solid was collected by filtration through a sintered funnel, washed with EtOAc (1 L) and dried for 18 h at 40° C. under vacuum to give the title compound (418.75 g, 78%). (Method 1) 97.45%, Rt 10.06 min.; 2.54%, Rt 14.67 min.; e.e. 94.91%. (Method 3) 96.69%, Rt 15.72 min.; 3.31%, Rt 17.78 min.; e.e. 93.38%. LCMS (Method 4) Rt 2.88 min, m/z 357 [MH$^+$—HCl], 99.55%. $^1$H NMR (400 MHz, DMSO-d$_6$): δ 12.0 (1 H, s), 8.70 (1 H, d, J 1.7 Hz), 8.36 (1 H, bd, J 8.3 Hz), 7.93 (1 H, d, J 8.2 Hz), 7.15, 6.87 (4H, A2B2q, J 8.7 Hz), 4.86 (1 H, dd, J 4.4, 8.9 Hz), 4.38 (2 H, t, J 6.3 Hz), 3.44 (2 H, t, J 6.2 Hz), 3.29 (1 H, dd, J 4.3, 14.2 Hz), 3.06 (1 H, dd, J 9.0, 14.3 Hz), 2.78 (2 H, q, J 7.6 Hz), 1.23 (3 H, t, J 7.6 Hz).

Example 19

(5R)-5-{4-[2-(5-ethylpyridin-2-yl)ethoxy]benzyl}-1,3-thiazolidine-2,4-dione L-tartrate

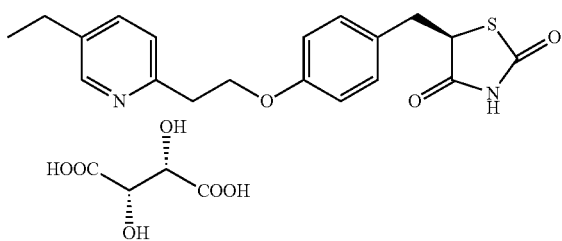

To a solution of L-tartaric acid (2.52 g) in THF (12 mL) at 35° C. was added (5R)-5-{4-[2-(5-ethylpyridin-2-yl)ethoxy]benzyl}-1,3-thiazolidine-2,4-dione(−)-O,O'-dibenzoyl-L-tartrate (2.0 g, d.e. >99%) to give a suspension which was allowed to cool to ambient temperature. After 90 min, the solid was collected by filtration, washed with 15 mL of THF at 0° C. and dried under vacuum to give (5R)-5-{4-[2-(5-ethylpyridin-2-yl)ethoxy]benzyl}-1,3-thiazolidine-2,4-dione L-tartrate which contained 0.5 eq THF by NMR analysis (2.06 g). This product (1.0 g) was added to a solution of L-tartaric acid (1.11 g) in MeOH (10 mL) at reflux and then allowed to cool to ambient temperature with seed crystals of (5R)-5-{4-[2-(5-ethylpyridin-2-yl)ethoxy]benzyl}-1,3-thiazolidine-2,4-dione L-tartrate (~5 mg). The solid was collected by filtration, washed with 2×5 ml MeOH at 0° C. and dried under vacuum. (Method 14) 99.25%, Rt 16.22 min.; 0.75%, Rt 18.47 min.; d.e. 98.5%. (Method 2) Rt 2.87 min m/z 357 [M-C$_4$H$_6$O$_4^+$]. $^1$H NMR (400 MHz, DMSO-d$_6$): δ 1.17 (3 H, t, J 7.4), 2.58 (2H, q, J 8.0), 3.04 (1H, dd, J 5.5, 14.2), 3.12 (2H, t, J 6.8), 3.29 (1H, dd, J 4.3, 14.2), 4.27-4.34 (4H, m), 4.86 (1H, dd, J 4.4, 9.1), 6.86 (2H, d, J 8.6), 7.13 (2H, d, J 8.6), 7.26 (1H, d, J 7.8), 7.57 (1H, dd, J 2.6, 8.3), 8.35-8.37 (1H, m).

Example 20

(5R)-5-{4-[2-(5-ethylpyridin-2-yl)ethoxy]benzyl}-1,3-thiazolidine-2,4-dione tosylate

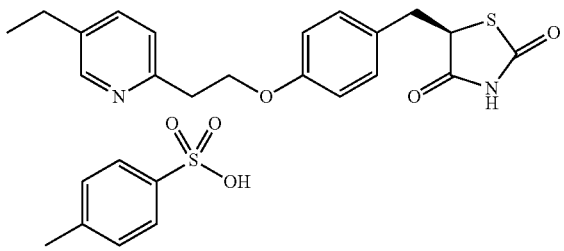

To a solution of p-toluenesulphonic acid (0.8 g) in IPA (12 mL) at 40° C. was added (5R)-5-{4-[2-(5-ethylpyridin-2-yl)ethoxy]benzyl}-1,3-thiazolidine-2,4-dione(−)-O,O'-dibenzoyl-L-tartrate (2.0 g, d.e. >99%) to give a suspension which was allowed to cool to ambient temperature. After 30 min, the solid was collected by filtration, washed with 5 ml of IPA at 0° C. and dried under vacuum to give the title compound (1.32 g). (Method 14) 99.41%, Rt 15.49 min.; 0.59%, Rt 17.52 min.; e.e. 98.82%. (Method 2) Rt 2.88 min, m/z 357 [M-C$_7$H$_8$SO$_3^+$]. $^1$H NMR (400 MHz, DMSO-d$_6$): δ 1.23 (3H, t, J 8.2), 2.28 (3H, s), 2.76 (2H, q, J 7.4), 3.05 (1H, dd, J 8.8, 14.0), 3.28 (1H, dd, J 4.1, 14), 3.38 (2H, t, J 5.9), 4.35 (2H, t, J 5.9), 4.86 (1H, dd, J 4.4, 9.1), 6.86 (2H, d, J 8.8), 7.12 (4H, dd, J 8.6, 16.6), 7.47 (2H, d, J 8.8), 7.90 (1H, d, J 8.3), 8.30 (1H, d, J 8), 8.68-8.71 (1H, m).

Comparative Example 1

In Example 15, Steps 2 and 3 acid was included in the methanol solvent for recrystallisation of the R-enantiomer as the chiral salt. The following comparative Example shows that omission of the acid results in recovery of the free base as an enantiomeric mixture rather than the required R enantiomer of the chiral salt:

A solution of L-DBTA (10.0 g, 27.9 mmol) and 5-{4-[2-(5-ethylpyridin-2-yl)ethoxy]benzyl}-1,3-thiazolidine-2,4-dione hydrochloride (10.0 g, 25.2 mmol) in MeOH (200 mL) was stirred at ambident temperature and H$_2$O (200 mL) was added over 10 min. When addition was complete, seed crystals from Preliminary Example 2 (5 mg) were added and the reaction allowed to stir for 56 h. The reaction was filtered and the solid dried to give (5R)-5-{4-[2-(5-ethylpyridin-2-yl)ethoxy]benzyl}-1,3-thiazolidine-2,4-dione(−)-O,O'-dibenzoyl-L-tartrate (8.41 g). (Method 1) 81.93%, Rt 10.18 min.; 18.06%, Rt 14.55 min.; d.e. 63.87%.

To the resultant product (100 mg) was added MeOH (0.98 mL). Water (0.57 mL) was added and the reaction allowed to stir for 24 h. The solid was collected by filtration, washed with MeOH—H$_2$O (1:2, 0.5 mL), and dried at 40° C. under high vacuum to give (5R)-5-{4-[2-(5-ethylpyridin-2-yl)ethoxy]benzyl}-1,3-thiazolidine-2,4-dione free base as an enantiomeric mixture. (Method 7) 62.28%, Rt 8.48 min.; 37.71%, Rt 13.52 min e.e. 24.5%. $^1$H NMR (400 MHz, DMSO-d$_6$): δ 1.17 (t, J=8.08 Hz, 3H), 2.58 (q, J=8.08 Hz, 2H), 3.04 (dd, J=10.44, 13.8 Hz, 1H), 3.12 (t, J=8.09 Hz, 2H), 3.27 (m, 1H), 4.29 (t, J=8.09, 2H), 4.85 (dd, J=4.62, 8.09 Hz, 1H), 6.86 (d, J=9.24 Hz, 2H), 7.13 (d, J=9.24 Hz, 2H), 7.26 (d, J=8.09 Hz, 1H), 7.56 (dd, J=2.46, 5.75 Hz, 1H), 8.36 (m, 1H).

Methods generally known which might successfully resolve the enantiomers of pioglitazone include the following categories:

Chiral chromatography
Chiral hydrogenation of an unsaturated intermediate
Enzyme/microbial mediated reduction of an unsaturated intermediate
Deprotonation/Chiral reprotonation
Separation of disastereomeric salts of glitazones
Chiral synthesis One of the key requirements for drug development is the provision of a scalable chemical process to supply large quantities of drug substance in order to be able to initially assess a molecule in pre-clinical and clinical studies. Subsequently a manufacturing process to enable a successful commercial endeavour is required.

Chiral Chromatography

Even though it was demonstrated (WO 2010/015818) on a small scale that chiral HPLC successfully separated pioglitazone into its constituent enantiomer forms, this technique cannot be used on a larger scale as the larger volumes of eluents and the subsequent increase in time to evaporate the solvent results in a larger degree of racemisation during the isolation process. It would not be feasible to produce large quantities of R-pioglitazone with the desired chiral purity (>90% ee) by this technique.

Other techniques were tried during the evaluation process leading to the present invention, as described in the Comparative Examples below, but were found unsatisfactory for various reasons:

Comparative Example 2

Catalytic chiral hydrogenation attempts to form (5R)-5-{4-[2-(5-ethylpyridin-2-yl)ethoxy]benzyl}-1,3-thiazolidine-2,4-dione

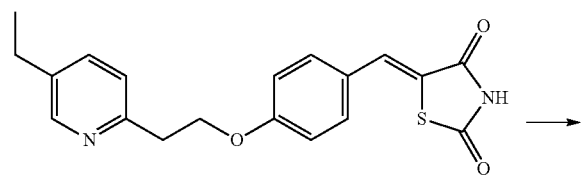

-continued

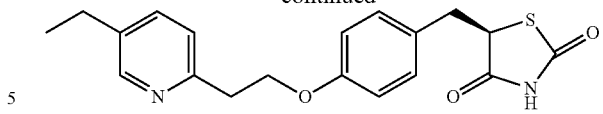

A stock solution of the Rh(COD)$_2$BF$_4$ (10.6 mg, 26.1 μmol) in DCM (9.5 mL) was made in a glove box. Ligand SL-W003-2 ((S)-1-[(S)-2-(2i-diphenylphosphinophenyl)ferrocenyl]ethyl-dicyclohexyl phosphine) (8.4 mg, 12.5 μmol), was weighed into a vial and 500 μL of the Rh(COD)$_2$BF$_4$ stock solution was added. A solution of 5-[1-{4-[2-(5-ethyl-pyridin-2-yl)-ethoxy]-phenyl}-meth-(E)-ylidene]-thiazolidine-2,4-dione (4.5 mL of a stock solution containing 78.2 mg in 35 mL MeOH) was added to the reaction vial containing the catalyst solution. The vial was purged with N$_2$ (5×) and H$_2$ (5×) and finally charged with 25 bar of H$_2$. After 18 h the H$_2$ was released and the reaction vial was purged with N$_2$ (3×). A sample of the reaction vial was taken and diluted with an equal volume of EtOH containing 1% formic acid. e.e. (Method 4) 75%, Rt 36.11 min, conversion 50%.

Asymmetric hydrogenations using rhodium, iridium and ruthenium catalysts were extensively explored with a variety of chiral ligands. Low conversion was observed together with low e.e. probably due to poor solubility of 5-[1-{4-[2-(5-ethyl-pyridin-2-yl)-ethoxy]-phenyl}-meth-(E)-ylidene]-thiazolidine-2,4-dione in various solvents. Addition of acid such as HCl or formic acid to give better solubility was also explored without improved outcome of the reactions. Because of the low conversion rate and poor enantiomeric purity achieved, this process was not considered suitable for scale up.

Comparative Example 3

Biocatalytic reduction attempts to form (R)-5-{4-[2-(5-ethyl-pyridin-2-yl)-ethoxy]-benzyl}-thiazolidine-2,4-dione Biocatalytic reduction of 5-[1-{4-[2-(5-ethyl-pyridin-2-yl)-ethoxy]-phenyl}-meth-(E)-ylidene]-thiazolidine-2,4-dione was investigated using literature procedures described for Rosiglitazone (*J. Chem. Soc. Perkin Trans. I*, 1994, 3319-3324).

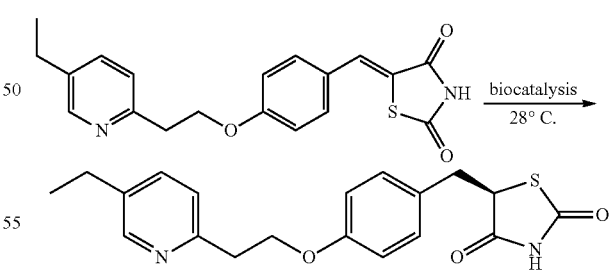

The wild type yeast strain *Rhodotorula glutinis* (CBS4406, IFO415 (DS14009)) was grown as described in *J. Chem. Soc. Perkin Trans. I*, 1994, 3319-3324. The exact *Rhodotorula rubra* strain used in this publication was not available and *Rhodotorula rubra* (or *mucilaginosa*) (ATCC4056, CBS2378, IFO911 (DS1332) was used instead and grown as described. One litre cultures using the same medium described in the publication were incubated with the yeast strains and grown for 72 hr before being harvested.

In addition to the yeast strains described above, an ene reductase-1 biocatalysis platform was screened. This ER-1 biocatalysis platform contained 29 ene reductases (available as a kit from DSMZ, Deutsche Sammlung von Mikroorganismen and Zellkulturen GmbH, Inhoffenstraße 7 B, 38124 Braunschweig, Germany) and were cultured in micro titre plate, cells were harvested by centrifugation and stored at −80° C. until required). For the screening, a cell pellet was used instead of the isolated enzymes because these were expected to be more stable in an acidic media than the isolated enzymes.

For screening, 32.5 mg of wet yeast cells (*Rhodotorula rubra* and *rodotorula glutinis*) were suspended in 1 mL of formate buffer. The enone reductases from the platform were suspended in 400 μL of formate buffer (50 mM pH 3.75, containing 0.05% sucrose) and 2.5 mg/mL of cofactor was added. The biocatalytic reactions were started by addition of 5-[1-{4-[2-(5-ethyl-pyridin-2-yl)-ethoxy]-phenyl}-meth-(E)-ylidene]-thiazolidine-2,4-dione (48 μL of a 23.4 mg/mL solution in dioxane). The micro titre plates were sealed and incubated at 28° C. while shaking.

After 2, 4 and 20 hours of incubation, samples of the ene reductase reactions were taken and diluted with ethanol (1.6 mL, containing 0.5% formic acid). The resulting mixtures were centrifuged and the supernatant was transferred into HPLC vials and analyzed by chiral HPLC. A reference standard containing only 5-[1-{4-[2-(5-ethyl-pyridin-2-yl)-ethoxy]-phenyl}-meth-(E)-ylidene]-thiazolidine-2,4-dione in the buffer/dioxane mixture was also analyzed. This sample contained a precipitate, confirming previous observations in our work, that 5-[1-{4-[2-(5-ethyl-pyridin-2-yl)-ethoxy]-phenyl}-meth-(E)-ylidene]-thiazolidine-2,4-dione in the buffer/dioxane mixture has low solubility. Chiral HPLC measurements showed no conversion for any of the ene reductases and yeast strains tested.

The yeast reactions were also run on a larger scale using 5-[1-{4-[2-(5-ethyl-pyridin-2-yl)-ethoxy]-phenyl}-meth-(E)-ylidene]-thiazolidine-2,4-dione (100 mg in 12 mL solvent) and were performed at different pH (pH=8.0; 3.75; 3.0) using two different organic solvents (dioxane and nBuOH) with three different buffer solutions. Buffers used were Tris.HCl buffer (100 mM, pH 8.0) containing 5% sucrose; citrate buffer (100 mM, pH 3.0) containing 5% sucrose and formate buffer (50 mM, pH 3.75) containing 5% sucrose. The yeast cells were suspended in the buffer solutions, giving a concentration of ~32.5 mg of wet yeast cells in 1 mL of buffer. On average ~0.8 g of wet yeast cells were used per reaction. 12 v/v % of organic solvent (containing 5-[1-{4-[2-(5-ethyl-pyridin-2-yl)-ethoxy]-phenyl}-meth-(E)-ylidene]-thiazolidine-2,4-dione) was added and the reactions mixtures were shaken overnight at 28° C. After shaking, the reaction mixtures were centrifuged and the supernatant was partially evaporated under reduced pressure at room temperature. The supernatant was basified to ~pH 8, using a 10% aqueous ammonia solution. The mixture was rapidly extracted with $CH_2Cl_2$ and the organic layer was evaporated under reduced pressure at room temperature. The residue was dissolved in ethanol containing 0.5% formic acid and analyzed by chiral HPLC. The aqueous layer was analysed by HPLC-TOF and only the starting material, 5-[1-{4-[2-(5-ethyl-pyridin-2-yl)-ethoxy]-phenyl}-meth-(E)-ylidene]-thiazolidine-2,4-dione, was observed.

No conversion to pioglitazone was observed for any of the biocatalytic reductions using the yeast enzyme systems described or a selection of ene reductases.

Comparative Example 4

Asymmetric synthesis of (5R)-5-{4-[2-(5-ethylpyridin-2-yl)ethoxy]benzyl}-1,3-thiazolidine-2,4-dione Hydrochloride 4a. Methanesulfonic acid 2-(5-ethyl-pyridin-2-yl)-ethyl ester

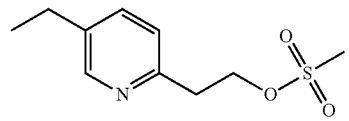

To a solution of 2-(5-ethyl-pyridine-2-yl)-ethanol (25.34 g) and triethylamine (46.7 mL) in DCM (130 mL) at 0° C. under nitrogen was added methane sulfonyl chloride (15.56 mL), then the reaction mixture was allowed to warm to room temperature and stirred overnight. A further portion of methane sulfonyl chloride (3.88 mL) was added and the reaction stirred for 30 min. The reaction was diluted with DCM and washed with $H_2O$ and brine. The organic layer was dried ($MgSO_4$) and the solution concentrated to give the title compound as a red oil (38.24 g). $^1$H NMR (400 MHz, $CDCl_3$): δ 8.39 (d, J=2.2 Hz, 1H), 7.47 (dd, J=7.7, 2.3 Hz, 1H), 7.14 (d, J=7.7 Hz, 1H), 4.64 (t, J=6.5 Hz, 2H), 3.19 (t, J=6.5 Hz, 2H), 2.90 (s, 3H), 2.64 (q, J=7.6 Hz, 2H), 1.25 (t, J=7.6 Hz, 3H).

4b. 3-{4-[2-(5-Ethyl-pyridin-2-yl)-ethoxy]-phenyl}-propionic acid methyl ester

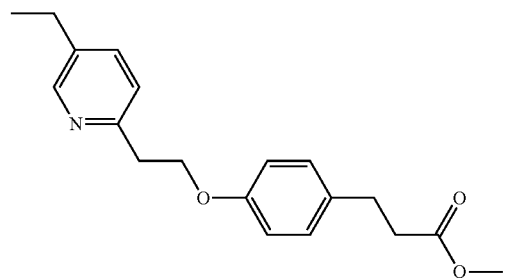 [SMILES: CCc1ccc(CCOc2ccc(CCC(=O)OC)cc2)nc1]

The product from Example 4a (12.72 g) in toluene (50 mL) was added dropwise to a stirred mixture of methyl-3-(4-hydroxyphenyl)propionate (10 g) and potassium carbonate (23.01 g) in toluene (180 mL). The reaction was heated to reflux for 23 h, then left at room temperature for 90 h. The reaction mixture was treated with $H_2O$ and extracted with three portions of diethyl ether. The combined extracts were washed twice with $H_2O$, once with brine, dried and evaporated. The residue was purified by chromatography eluting with 20-40% EtOAc in petroleum ether (bp=40-60° C.) to give the title product as a yellow solid (10.73 g). $^1$H NMR (400 MHz, $CDCl_3$): δ 8.39 (d, J=2.1 Hz, 1H), 7.44 (dd, J=7.8, 2.4 Hz, 1H), 7.18 (d, J=7.8 Hz, 1H), 7.08, 6.83 ($A_2B_2$q, J=8.6 Hz, 4H), 4.31 (t, J=6.7 Hz, 2H), 3.66 (s, 3H), 3.22 (t, J=6.7 Hz, 2H), 2.87 (t, J=7.6 Hz, 2H), 2.66-2.55 (m, 4H), 1.24 (t, J=7.6 Hz, 3H).

4c. 3-{4-[2-(5-Ethyl-pyridin-2-yl)-ethoxy]-phenyl}-propionic acid

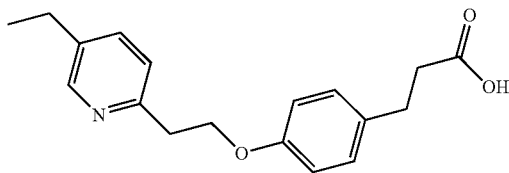 [SMILES: CCc1ccc(CCOc2ccc(CCC(=O)O)cc2)nc1]

The product from Example 4b (10.73 g) was dissolved in 1,4-dioxan/H$_2$O (350/100 mL), lithium hydroxide monohydrate (4.3 g) added, and the reaction stirred overnight. The dioxan was removed by evaporation under reduced pressure, the suspension was diluted with H$_2$O and treated with 2.0 M HCl until the pH was 6-7. The solid was filtered and dried to give the title compound (9.57 g). $^1$H NMR (400 MHz, CDCl$_3$): δ 8.41 (d, J=2.3 Hz, 1H), 7.52 (dd, J=7.9, 2.3 Hz, 1H), 7.25 (d, J=7.9 Hz, 1H), 7.11, 6.81 (A$_2$B$_2$q, J=8.6 Hz, 4H), 4.27 (t, J=6.6 Hz, 2H), 4.0 (bs, 2 H, COOH+H$_2$O) 3.24 (t, J=6.6 Hz, 2H), 2.90 (t, J=7.6 Hz, 2H), 2.68-2.59 (m, 4H), 1.24 (t, J=7.6 Hz, 3H).

4d. (R)-4-Benzyl-3-(3-{4-[2-(5-ethyl-pyridin-2-yl)-ethoxy]-phenyl}-propionyl)-oxazolidin-2-one

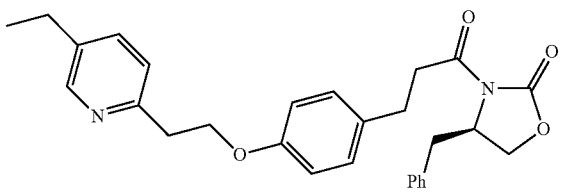 [SMILES: CCc1ccc(CCOc2ccc(CCC(=O)N3C(=O)OC[C@H]3Cc3ccccc3)cc2)nc1]

A suspension of the product from Example 4c (9.0 g) and (R)-(+)-4-benzyloxazolidinone (2.67 g) in triethylamine (8.38 mL) and toluene (90 mL) was heated to 80° C. Pivaloyl chloride (3.71 mL) was added dropwise maintaining the temperature between 80 and 85° C. The reaction was then heated to reflux for 22.5 h. The reaction was allowed to cool to room temperature, partitioned between H$_2$O-EtOAc and the aqueous layer was extracted twice with EtOAc and the combined organics dried (MgSO$_4$) and concentrated. The crude product was purified by chromatography on silica gel eluting with 0-40% EtOAc-cyclohexane to give the title product as a white solid (2.06 g). $^1$H NMR (300 MHz, CDCl$_3$): δ 8.39 (d, J=2.2 Hz, 1H), 7.45 (dd, J=7.9, 2.2 Hz, 1H), 7.36-7.24 (m, 3H), 7.21-7.12 (m, 5H), 6.84 (d, J=8.6 Hz, 2H), 4.65 (m, 1H), 4.32 (t, J=6.6 Hz, 2H), 4.16 (m, 2H), 3.33-3.12 (m, 5H), 3.04-2.87 (m, 2H), 2.74 (dd, J=9.5, 13.4 Hz, 1H), 2.63 (q, J=7.6 Hz, 2H), 1.24 (t, J=7.6 Hz, 3H).

4e. (R)-4-Benzyl-3-((R)-3-{4-[2-(5-ethyl-pyridin-2-yl)-ethoxy]-phenyl}-2-thiocyanato-propionyl)-oxazolidin-2-one

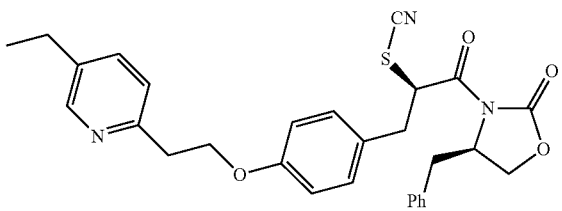 [SMILES: CCc1ccc(CCOc2ccc(C[C@@H](SC#N)C(=O)N3C(=O)OC[C@H]3Cc3ccccc3)cc2)nc1]

To LDA (0.528 mmol) in THF/hexanes (3/0.3 mL) at −78° C. under argon was added dropwise the product from Example 4d (0.20 g) in THF (4 mL). After 30 min N-thiocyanatosuccinimide (*JACS*, 2004, 126, 10216-7) (0.137 g) in THF (2 mL) was added dropwise. After a further 110 min at −78° C. the reaction was quenched with sat aqueous NH$_4$Cl (5 mL) and allowed to warm to room temperature. The mixture was extracted with three 15 mL portions of EtOAc, the combined organic layers were dried (Na$_2$SO$_4$) and evaporated under reduced pressure to low volume. Toluene (20 mL) was added and evaporated under reduced pressure. The residue was dissolved in DCM (3 mL) and stored at −20° C. for 16 h. The soluble material was purified by chromatography on silica gel eluting with 20-50% EtOAc in cyclohexane, repurifying impure fractions by the same method, to give the title product and succinimide in 1:2.4 molar ratio as a colourless semi solid (0.121 g). $^1$H NMR (300 MHz, CDCl$_3$): δ 8.60 (bs, 1H succinimide) 8.40 (d, J=2.3 Hz, 1H), 7.47 (dd, J=7.8, 2.3 Hz, 1H), 7.39-7.12 (m, 8H), 6.85 (d, J=8.7 Hz, 2H), 5.07 (dd, J=8.1, 7.2 Hz, 1H), 4.63 (m, 1H), 4.32 (t, J=6.7 Hz, 2H), 4.24-4.11 (m, 2H), 3.47 (dd, J=14.0, 8.0 Hz, 1H), 3.33 (dd, J=13.4, 3.2 Hz, 1H), 3.28-3.16 (m, 3H), 2.84 (dd, J=9.3, 13.4 Hz, 1H), 2.76 (s, 4H succinimide) 2.63 (q, J=7.6 Hz, 2H), 1.24 (t, J=7.6 Hz, 3H).

4f. Thiocarbamic acid S—((R)-2-((R)-4-benzyl-2-oxo-oxazolidin-3-yl)-1-{4-[2-(5-ethyl-pyridin-2-yl)-ethoxy]-benzyl}-2-oxo-ethyl)ester

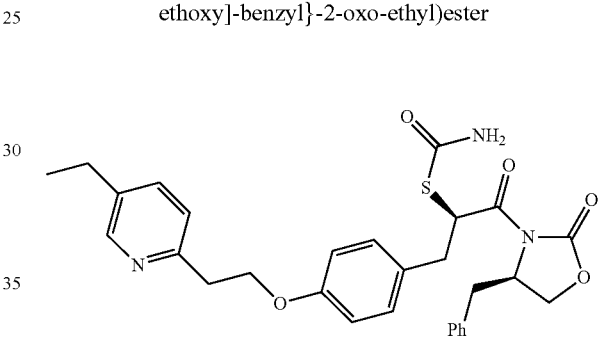

The product from Example 4e (51 mg) was dissolved in THF/H$_2$O (2/1 ml) under argon and treated with platinum tris(dimethylphosphine oxide) (*Tet. Lett.*, 2002, 43, 8121) (4 mg). The reaction was warmed to 40° C. for 2 h then allowed to cool to room temperature. EtOAc (10 mL) was added, the organic phase dried (Na$_2$SO$_4$), concentrated and purified by chromatography on silica gel (2 g) eluting with 40-70% EtOAc in cyclohexane to give the title product and succinimide in 1:3.3 molar ratio as a colourless semi solid (0.029 g). $^1$H NMR (400 MHz, CDCl$_3$): δ 8.66 (bs, 1H succinimide) 8.39 (d, J=2.0 Hz, 1H), 7.47 (dd, J=7.9, 2.2 Hz, 1H), 7.37-7.17 (m, 6H), 7.17, 6.81 (A$_2$B$_2$q J=8.5 Hz, 4H), 5.74 (t, J=7.9 Hz, 1H), 5.63 (bs, 2H), 4.53 (m, 1H), 4.30 (t, J=6.7 Hz, 2H), 4.08 (dd, J=8.9, 2.5 Hz, 1H), 3.95 (dd, J=8.9, 7.8 Hz, 1H), 3.31 (dd, J=13.5, 3.1 Hz, 1H), 3.26-3.18 (m, 3H), 2.96 (dd, J=13.5, 8.1 Hz, 1H), 2.74 (s, 4H succinimide), 2.72 (dd, J=13.5, 9.8 Hz, 1H), 2.63 (q, J=7.6 Hz, 2H), 1.24 (t, J=7.6 Hz, 3H).

4g. (5R)-5-{4-[2-(5-ethylpyridin-2-yl)ethoxy]benzyl}-1,3-thiazolidine-2,4-dione hydrochloride (2)

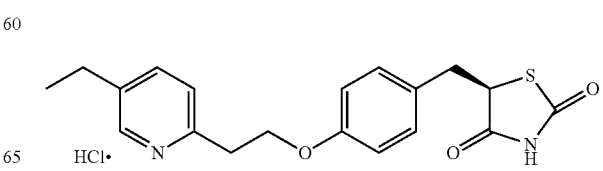

The product from Example 4f was dissolved in MeOH (10 mL) and H$_2$O (10 ml) added to give a cloudy solution. This was left at room temperature for 2.5 h then 1M HCl (0.15 mL) added. The solution was evaporated to dryness and the residue taken up in MeOH (0.1 mL) containing concentrated HCl (0.0015 mL). EtOAc (5 mL) was added and the solution concentrated slightly under reduced pressure, causing a white solid to precipitate. The solution was removed and the solid (7 mg) washed with EtOAc. This material was purified by preparative HPLC (Method 5), and the fractions containing the first eluting component combined and treated with 1M HCl (1 mL) and evaporated to dryness to give the title product and succinimide in a 1:0:0.19 molar ratio as a colourless gum (0.002 g). (Method 1) 99.175%, Rt 10.65 min.; 0.825%, Rt 14.83 min.; e.e. 98.35%. LCMS (Method 11) Rt 2.9 min, m/z 357 [MH$^+$]. $^1$H NMR (300 MHz, d$_4$-MeOH): δ 8.62 (bd, 1H), 8.42 (dd, J=8.2, 2.0 Hz, 1H), 7.98 (d, J=8.2 Hz, 1H), 7.16, 6.85 (A$_2$B$_2$q, J=8.7 Hz, 4H), 4.68 dd, J=8.7, 4.2 Hz, 1H), 4.38 (t, J=5.8 Hz, 2H), 3.34 (m obscured, 1H), 3.11 (dd, J=14.3, 8.8 Hz, 1H), 2.87 (q, J=7.6 Hz, 2H), 2.68 (s, 4H succinimide), 1.33 (t, J=7.6 Hz, 3H).

This method is not suitable to provide commercially viable quantities of R-pioglitazone because the material had to be isolated from the final crude reaction mixture by preparative HPLC, step 4 requires a highly pyrophoric catalyst, and a platinum catalyst is extremely expensive.

Comparative Example 5

Attempts to prepare (5R)-5-{4-[2-(5-ethylpyridin-2-yl)ethoxy]benzyl}-1,3-thiazolidine-2,4-dione by deprotonation-chiral protonation of pioglitazone The preparation of enantiomerically pure pioglitazone was investigated using chiral re-protonation of deprotonated pioglitazone. This approach has been described (L. Duhamel, J.-C. Plaquevent, *JACS.,* 1978, 100, 7415).

The following example is a representative procedure. Pioglitazone (180 mg, 0.5 mmol) was dissolved in 5 mL THF and treated with LiOH (12 mg). The mixture was stirred for 30 minutes and divided in 5 test tubes. The test tubes were cooled at −40° C. and to each test tube was added 0.1 mmol of the following acids; L-ditoluoyl tartaric acid, (R) or (S) anicyphos, (S) camphor sulfonic acid, (R) chalcone sulfonic acid 4 (R=H) and 1,1'-binaphthyl-2,2'-diyl hydrogen phosphate. The solution was allowed to warm up to RT. The precipitated pioglitazone was collected and directly analyzed by chiral HPLC.

Four series of experiments were set up to investigate deprotonation of the thiazolidinedione ring of pioglitazone with LDA, LiOH, KOH or triton B in THF and methanol. The re-protonation using the acids above was started at several temperatures from −40° C. to 0° C. At lower temperature the deprotonated pioglitazone sometimes precipitated. After re-protonation, the precipitated pioglitazone was collected and analysed by chiral HPLC which showed that only racemic material had precipitated. It was therefore concluded that this technique could not be used for production of R-pioglitazone.

Use of Chiral Amines

Since pioglitazone contains an acidic moiety a range of chiral amine resolving agents were utilised.

Comparative Example 6

Attempts to Resolve Pioglitazone Using Chiral Amines

Literature separation of glitazones using diastereomeric salts has previously been accomplished using chiral bases. Ciglitazone and MK-0767 were converted into their enantiomers using (R)-(+)-1-phenylethylamine or (S)-(−)-1-phenylethylamine and good chiral purity was obtained (T. Sohda et. al., *Chem. Pharm. Bull.* 1984, 32(11), 4460; Z. Shen et. al., *Rapid Commun. Mass Spectroscopy.* 2005, 19, 1125; T Doebber et. al., *Biochem. Biophysical Research Communication,* 2004, 318, 323; R Rippley et. al., *J Clin. Pharmacol.,* 2007, 47, 323). Rosiglitazone was separated into the S-enantiomer using quinine (B. C. C Cantello et. al., *J. Chem. Soc. Perkin Trans. I,* 1994, 3319-3324; Parks et. al., 1998, *Bioorg. Med. Chem. Lett.* 8(24), 3657-8).

Initially, resolution of pioglitazone was attempted with (R)-(+)-1-phenylethylamine but this failed. Subsequently additional basic resolving agents were also investigated: cinchonidine, cinchonine, quinidine, quinine, (−)-ephedrine, (R)-amino butanol, (+)-dehydroabiethylamine, (S)-2-phenyl glycinol, (R,R)-1,2-cyclohexyldiamine, (R,R)-2-amino-1-phenylpropane-1,3-diol, (R)-4-chloro-1-phenylamine, (+)-N-(4-methoxybenzyl)-1-phenylethyl amine, (1S)-fenchylamine, (+)-N-benzyl-1-phenylethyl amine, (+)-N-(4-dimethylaminobenzyl)-1-phenylethyl amine and (+)-3-amino-2,2-dimethyl-3-phenylpropan-1-ol. A stronger base, sparteine was used as well. Furthermore, chiral amino acids incorporating a basic group were screened: L-lysine, L-arginine, L-homo-arginine. The resolution reactions were assessed using a range of solvents:: 10% HCl in H$_2$O, H$_2$O, DMF, 10% H$_2$O in DMF, EtOH, 10% H$_2$O in EtOH, IPA, 10% H$_2$O in IPA, 1-butanol, 2-butanone, ethyl acetate and toluene.

The precipitates from each experiment were studied by NMR but with the exception of L-lysine, none showed evidence of salt formation. High crystallinity and low solubility of pioglitazone, which often precipitates out quickly from the reaction mixture, hampers salt formation. Resolution with lysine in 1-butanol, provided some chiral separation (Comparative Example 7) but this was very irreproducible, low yielding and not suitable for scale up.

General Screening Procedure for the Formation of Diastereomeric Salts of Pioglitazone with Chiral Amines To 5-{4-[2-(5-ethylpyridin-2-yl)ethoxy]benzyl}-1,3-thiazolidine-2,4-dione (20-100 mg) was added 1 equivalent of chiral base followed by solvent (1-15 mL). Chiral bases used included brucine, (+)-cinchonin, (R)-(+)-1-phenylethylamine, (+)-norephedrine, L-tyrosine methyl ester, (R)-(+)-1-(1-naphthyl)ethylamine, arginine and quinidine in combination with solvents including CH$_3$CN, 1-butanol, toluene, 1,4-dioxane, acetone, methylisobutylketone, methyl ethyl ketone, 1,2-dichloroethane, morpholine, pyridine, DME, EtOH, EtOAc, IPA, MeOH, 70% IPA-H$_2$O, 80% MeOH—H$_2$O. The reaction was heated up to the reflux temperature of the solvent to dissolve solids, filtered through a cotton wool plug to remove un-dissolved material and the hot, saturated solutions allowed to cool to ambient temperature and allowed to stand. Any solid which formed on standing up to 2 weeks was collected by filtration and dried under vacuum. Analysis was completed using $^1$H NMR in DMSO-d$_s$ to look for formation of a salt of 5-{4-[2-(5-ethylpyridin-2-yl)ethoxy]benzyl}-1,3-thiazolidine-2,4-dione.

The precipitates from each experiment were studied by NMR but none showed evidence of salt formation. High crystallinity and low solubility of pioglitazone, which often precipitates out quickly from the reaction mixture, hampers salt formation.

Comparative Example 7

Procedure for the Attempted Formation of Diastereomeric Salts of Pioglitazone with L-Lysine To 5-{4-[2-(5-ethylpyridin-2-yl)ethoxy]benzyl}-1,3-thiazolidine-2,4-dione (100 mg, 0.28 mmol) was added L-lysine (41 mg, 0.28 mmol) followed by 1-butanol (3 mL) and the reaction taken to reflux temperature. Further 1-butanol was added until a clear solution was obtained at reflux, heating was continued for 15 minutes before the reaction was hot filtered. The filtrate was allowed to stand for 18 h at room temperature, the precipitate collected and dried under vacuum to give the title compound (15 mg). (Method 10) 79.0%, Rt 6.13 min.; 20.0%, Rt 9.31 min.; d.e. 60%. $^1$H NMR in CDCl$_3$ δ 0.94 (2H, t, J 8.4), 1.20-1.28 (6H, m), 1.33-1.45 (2H, m), 1.51-1.70 (4H, m), 2.63 (4H, q, J 8.4), 3.10 (2H, dd, J 4.5, 14.6), 3.22 (4H, dd, J 10.1, 14.1), 3.42 (2H, dd, J 10.1, 14.1), 3.65 (1H, t, J 6.7), 4.31 (4H, t, J 6.7), 4.47 (2H, dd, J 6.2, 9.0), 6.84 (4H, d, J 10.7), 7.11 (4H, d, J 10.7), 7.18 (2H, d, J 6.7), 7.45 (2H, dd, J 5.7, 7.8), 8.38-8.40 (2H, m). Salt to base ratio is 0.5:1.

This method provided some chiral separation but this was very irreproducible, with low recovery of salt and could not be successfully scaled up. Poor solubility of the pioglitazone in butanol contributed to these observations.

Comparative Example 8

Procedure for the Attempted Formation of Diastereomeric Salts of Pioglitazone with Quinine To 5-{4-[2-(5-ethylpyridin-2-yl)ethoxy]benzyl}-1,3-thiazolidine-2,4-dione (50 mg, 0.14 mmol) was added Quinine (0.14 mmol) followed by solvent (3-15 mL) selected from CH$_3$CN, 1-butanol, DME, EtOH, EtOAc, IPA and MeOH. The reaction was heated up to 70° C. to dissolve solids, filtered through a cotton wool plug to remove undissolved material and the hot, saturated solutions allowed to cool to ambient temperature and allowed to stand. Solids formed in all solvents except DME over 1-3 days and these were collected by filtration and dried under vacuum. Analysis using $^1$H NMR in DMSO-d$_6$ confirmed that only 5-{4-[2-(5-ethylpyridin-2-yl)ethoxy]benzyl}-1,3-thiazolidine-2,4-dione had been isolated as a free base. $^1$H NMR (400 MHz, DMSO-d$_6$): δ 12.44-11.11 (1 H, bs), 8.34-8.29 (1 H, d, J 1.9 Hz), 7.55-7.49 (1 H, dd, J 2.2, 7.9 Hz), 7.24-7.20 (1 H, d, J 7.8 Hz), 7.12-7.05 (2 H, d, J 8.6 Hz), 6.84-6.77 (2H, d, J 8.6 Hz), 4.78-4.71 (1 H, dd, J 4.3, 9.1 Hz), 4.30-4.19 (1 H, d, J 4.3 Hz), 3.24-3.18 (2 H, m), 3.11-3.03 (2 H, t, J 6.6 Hz), 3.00-2.92 (1 H, dd, J 9.2, 14.2 Hz), 2.59-2.50 (2 H, q, J 7.6 Hz), 1.17-1.09 (3 H, t, J 7.7 Hz).

Use of Chiral Acids

Since pioglitazone contains a basic pyridine moiety a range of chiral acid resolving agents were utilised. The general protocol below for use of (−)-di-o-tolyl-L-tartaric acid was adopted.

Comparative Examples 9

Chiral Sulphonic Acids (S)-camphor sulfonic acid, (S)-bromo camphorsulfonic acid, (+)-camphoric acid, (S)-phenylethyl sulfonic acid and (R)-chalcone sulfonic acids 4 did form a salt with pioglitazone but only in the case of chalcone sulfonic acid 4 (R═H) was a crystalline salt obtained, as assessed by nmr. No resolution was achieved by chiral HPLC analysis of the crystalline salt.

Comparative Example 10

Chiral Phosphoric Acids (R)-Phencyphos 3, (R)-chlocyphos 3, (R)-anicyphos 3,1, 1'-binaphthyl-2,2'-diyl hydrogen phosphate and P-mix 3 (Dutch resolution; T. Vries et. al., Angew. Chem. Int. Ed., 1998, 37, 2349; (S)-phencyphos, (S)-anicyphos, (S) chlocyphos) did form salts by NMR analysis but these did not crystallise and hence resolution was not achieved.

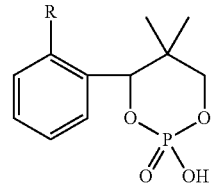

Phencyphos R = H
anicyphos R = MeO
Chlocyphos R = Cl
P-mix is 1:1:1 ratio

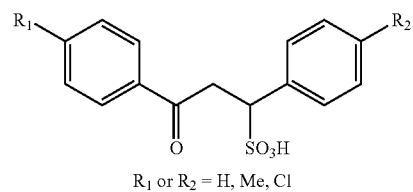

R$_1$ or R$_2$ = H, Me, Cl

Comparative Examples 11

Chiral Carboxylic Acids (−)O,O'-Dibenzoyl tartaric acid, (−)O,O'-di-p-anisoyl tartaric acid (Example 12), (−)O,O'-di-p-toluoyl tartaric acid (Example 10), L-tartaric acid (Example 11), D-tartaric acid, L-malic acid, (S)-mandelic acid, (S)-4-bromo mandelic acid, (S)-4-methyl mandelic acid, L-lactic acid, and M-mix (Dutch resolution, T. Vries et al, Angew. Chem. Int. Ed., 1998, 37, 2349 (S)-mandelic acid, (S)-4-bromo mandelic acid, (S)-4-methyl mandelic acid).

Under the conditions utilised none of the carboxylic acids formed salts with pioglitazone as assessed by NMR. Only crystallisation of pioglitazone free base was observed.

Comparative Example 12

Procedure for the attempted formation of diastereomeric salts of Pioglitazone with (−)-O,O'-di-p-toluoyl-L-tartaric acid, using the same methanol/water solvent system as used in the method of the invention (Example 1).

Preparation of (5R)-5-{4-[2-(5-ethylpyridin-2-yl) ethoxy]benzyl}-1,3-thiazolidine-2,4-dione(−)-O,O'-di-p-toluoyl-L-tartrate

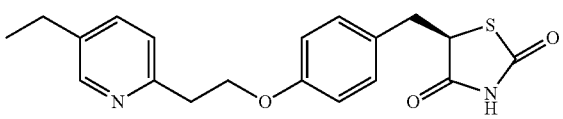

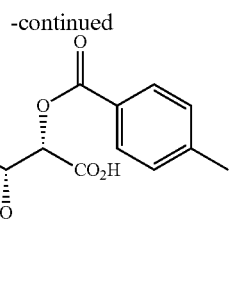

5-{4-[2-(5-ethylpyridin-2-yl)ethoxy]benzyl}-1,3-thiazolidine-2,4-dione hydrochloride (100 mg) in MeOH (2 mL) was stirred for 5 min. using brief sonication to give a clear solution. (−)-O,O'-di-p-toluoyl-L-tartaric acid (99 mg, 1 eq) was added followed by dropwise addition of water until a haziness persisted (up to 2 mL used). The reaction was stirred in closed vial for 96 h, the precipitated solid was collected on a filter cup and washed with H$_2$O-MeOH (2:1, 3 ml) and then dried under vacuum (123 mg). (Method 13) 44.55%, Rt 9.64 min.; 55.44%, Rt 14.86 min.; d.e. 10.89%. $^1$H NMR (400 MHz, DMSO-d$_6$): δ 1.17 (3H, t, J 7.7), 2.40 (6H, s), 2.58 (2H, q, J 8.1), 3.04 (2H, dd, J 4.8, 9.2), 3.12 (2H, t, J 7.0), 4.29 (2H, t, J 7.0), 4.86 (1H, dd, J 4.4, 4.0), 5.81 (2H, s), 6.86 (2H, d, J 9.2), 7.13 (2H, d, J 9.2), 7.27 (1H, d, J 7.4), 7.40 (4H, d, J 8.5), 7.58 (1H, dd, J 1.4, 7.7), 7.90 (4H, d, J 8.5), 8.35-8.37 (1H, m).

Although a salt formed with (−)-O,O'-di-p-toluoyl-L-tartaric acid in this experiment, the d.e. was very poor and not suitable for further scale up to give a suitable process route.

Comparative Example 13

Procedure for the attempted formation of diastereomeric salts of Pioglitazone with L-tartaric acid using the same methanol/water solvent system as used in the method of the invention (Example 1).

(5R)-5-{4-[2-(5-ethylpyridin-2-yl)ethoxy]benzyl}-1,3-thiazolidine-2,4-dione L-tartrate

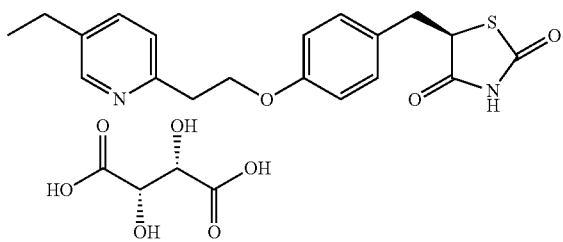

5-{4-[2-(5-ethylpyridin-2-yl)ethoxy]benzyl}-1,3-thiazolidine-2,4-dione hydrochloride (100 mg) in MeOH (2 mL) was stirred for 5 min. using brief sonication to give a clear solution. L-tartaric acid (38 mg, 1 eq) was added followed by dropwise addition of water until a haziness persisted (up to 2 mL used). The reaction was stirred in closed vial for 96 h, the precipitated solid was collected on a filter cup and washed with H$_2$O-MeOH (2:1, 3 ml) and then dried under vacuum (42 mg). (Method 13) 48.30%, Rt 9.62 min.; 51.60%, Rt 14.30 min.; d.e. 3.3%. $^1$H NMR (400 MHz, DMSO-d$_6$): δ 8.34-8.29 (1H, d, J 1.9), 7.55-7.49 (1 H, dd, J 2.2, 7.9), 7.24-7.20 (1 H, d, J 7.8), 7.12-7.05 (2 H, d, J 8.6), 6.84-6.77 (2 H, d, J 8.6), 4.78-4.71 (1 H, dd, J 4.3, 9.1), 4.30-4.19 (1 H, d, J 4.3), 3.24-3.18 (2 H, d), 3.11-3.03 (2 H, t, J 6.6), 3.00-2.92 (1 H, dd, J 9.2, 14.2), 2.59-2.50 (2 H, q, J 7.6), 1.17-1.09 (3 H, t, J 7.7).

Free base, racemic pioglitazone was isolated from this experiment making this unsuitable to develop a process route.

Comparative Example 14

Procedure for the attempted formation of diastereomeric salts of Pioglitazone with (−)-di-p-anisoyl-L-tartaric acid using the same methanol/water solvent system as used in the method of the invention (Example 1).

(5R)-5-{4-[2-(5-ethylpyridin-2-yl)ethoxy]benzyl}-1,3-thiazolidine-2,4-dione (−)-di-p-anisoyl-L-tartaric acid

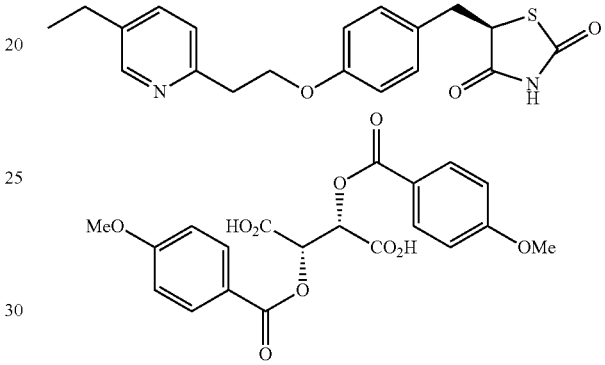

5-{4-[2-(5-ethylpyridin-2-yl)ethoxy]benzyl}-1,3-thiazolidine-2,4-dione hydrochloride (100 mg) in MeOH (2 mL) was stirred for 5 min. using brief sonication to give a clear solution. (−)-O,O'di-p-anisoyl-L-tartaric acid (106 mg, 1 eq) was added followed by dropwise addition of water until a haziness persisted (up to 2 mL used). The reaction was stirred in closed vial for 96 h, the precipitated solid was collected on a filter cup and washed with H$_2$O-MeOH (2:1, 3 ml) and then dried under vacuum (127 mg). (Method 13) 72.88%, Rt 9.75 min.; 27.11%, Rt 13.94 min.; d.e. 45.77%. $^1$H NMR (400 MHz, DMSO-d$_6$): δ 1.17 (3H, t, J 7.7), 2.58 (2H, q, J 8.1), 3.04 (2H, dd, J 4.8, 9.2), 3.12 (2H, t, J 7.0), 3.85 (6H, s), 4.29 (2H, t, J 7.0), 4.86 (1H, dd, J 4.4, 4.0), 5.81 (2H, s), 6.86 (2H, d, J 9.2), 7.10-7.16 (6H, m), 7.27 (1H, d, J 7.4), 7.58 (1H, dd, J 1.4, 7.7), 7.90 (4H, d, J 8.5), 8.35-8.37 (1H, m).

Although a salt formed with (−)-O,O'-di-p-anisoyl-L-tartaric acid in this experiment, the d.e. was poor and not suitable for further scale up to give a suitable process route.

Comparative Example 15

Preparation of (5R)-5-{4-[2-(5-ethylpyridin-2-yl)ethoxy]benzyl}-1,3-thiazolidine-2,4-dione(−)-O,O'-dibenzoyl-L-tartrate using CHCl$_3$/EtOAc as solvent (ie a different solvent system from that used in the method of the invention)

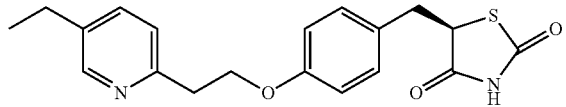 [SMILES: CCc1ccc(CCOc2ccc(C[C@H]3SC(=O)NC3=O)cc2)nc1]

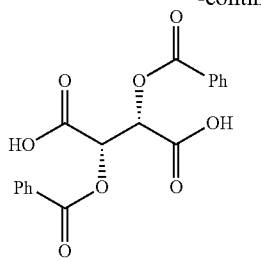

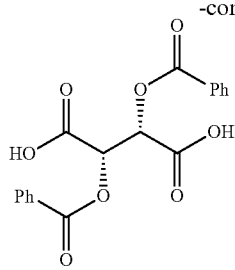

15a. To a solution of 5-{4-[2-(5-ethylpyridin-2-yl)ethoxy]benzyl}-1,3-thiazolidine-2,4-dione (5.0 g, 14.04 mmol) in CHCl₃ (37 mL) at room temperature, was added a slurry of L-DBTA (10.0 g, 28.08 mmol) in CHCl₃ (38 mL). The reaction mixture was stirred at room temperature for 10 min to give a gummy mass. The reaction was heated to reflux and after 5 min EtOAc (15 mL) was added. Heating was continued for 1 h, the reaction was slowly cooled to room temperature and filtered to give the title compound (8.1 g). d.e. (method 6) 20.84%; Rt 4.92 min 60.02%; Rt 8.21 min 39.98%.

15b. To a slurry of L-DBTA (8.1 g) in chloroform (40 mL) at room temperature was added the product from Example 15a (8.1 g) suspended in chloroform (40 mL). The reaction mixture was stirred at room temperature for 10 min to give a gummy mass. The reaction was heated to reflux and after 5 min EtOAc (16 mL) was added. Heating was continued for 1 h, the reaction was slowly cooled to room temperature and filtered to give the title compound (5.5 g). d.e. (method 6) 50.68%; Rt 4.92 min 75.34%; Rt 8.21 min 24.66%.

15c. The method described in Example 15b was repeated six times to give the title compound (0.6 g). d.e. (method 7) 94.14%; Rt 7.79 min 97.07%; Rt 11.48 min 2.93%. Mp 154-158° C. IR (KBr) 3437, 3392, 3113, 3051, 2972, 2891, 2775, 1915, 1728, 1703, 1598, 1554, 1510, 1452, 1390, 1350, 1334, 1317, 1298, 1246 cm⁻¹. ¹H NMR (400 MHz, DMSO-d₆) δ 14.25-13.60 (bs, 1 H, D₂O exchangeable), 12.05-12.00 (bs, 1 H, D₂O exchangeable), 8.37 (d, J=2.0 Hz, 1H), 8.02 (d, J=7.6 Hz, 4H), 7.73 (t, J=7.6 Hz, 2H), 7.60 (t, J=7.6 Hz, 5H), 7.29 (d, J=8.0 Hz, 1H), 7.13 (d, J=8.8 Hz, 2H), 6.86 (d, J=8.8 Hz, 2H), 5.88 (s, 2H), 4.86 (q, J=4.4 Hz, 1H), 4.30 (t, J=6.8 Hz, 2H), 3.30 (dd, J=4.0 & 10.0 Hz, 1H), 3.13 (t, J=6.8 Hz, 2H), 3.04 (dd, J=5.2 & 9.2 Hz, 1H), 2.60 (q, J=7.6 Hz, 2H), 1.17 (t, J=7.6 Hz, 3H). MS (Electrospray) 715 (M+1)⁺, 379, 360, 357, 286, 241, 134. [α]_D^{25} +4.61° (c 1.0, DMSO).

Although material with high e.e. could be obtained from this process, the overall isolated yield was very low. This results in a very inefficient process.

Comparative Example 16

Preparation of (5R)-5-{4-[2-(5-ethylpyridin-2-yl)ethoxy]benzyl}-1,3-thiazolidine-2,4-dione(−)-O,O'-dibenzoyl-L-tartrate using (3) CHCl₃/Dioxan as solvent

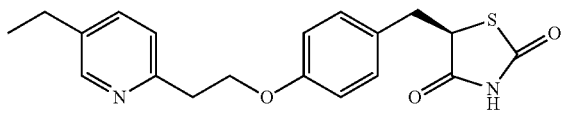

16a. A mixture of 5-{4-[2-(5-ethylpyridin-2-yl)ethoxy]benzyl}-1,3-thiazolidine-2,4-dione (10.0 g, 28.1 mmol) and L-DBTA (20 g, 56.2 mmol) in CHCl₃ (150 mL) was heated to an internal temperature of 55° C. 1,4-Dioxane (13 mL) was added over 1 h. The reaction was heated at 55° C. for 70 h and then 65° C. for 70 h. The reaction was slowly cooled to room temperature, filtered and the solid dried to give the title compound (8.11 g). d.e. (method 6) 66.4%; Rt 11.29 min., 83.2%; Rt 15.35 min., 16.8%.

16b. A mixture of 5-{4-[2-(5-ethylpyridin-2-yl)ethoxy]benzyl}-1,3-thiazolidine-2,4-dione (8.09 g, 11.32 mmol) and L-DBTA (8.10 g, 22.64 mmol) in CHCl₃ (120 mL) was heated to an internal temperature of 65° C. 1,4-Dioxane (12 mL) was added over 45 min. The reaction was heated at 65° C. for 18 h and was slowly cooled to room temperature, filtered and the solid dried to give the title compound (4.9 g). d.e. (method 6) 74.3%; Rt 11.29 min., 87.16%; Rt 15.35 min., 12.84%.

16c. The product from Example 16b was reacted twice as described in Example 14b to give the title compound (2.51 g). d.e. (method 6) 85.6%; Rt 11.29 min., 92.8%; Rt 15.35 min., 7.16%.

Although material with high e.e. could be obtained from this process, the overall yield was low. This results in a very inefficient process.

Comparative Example 17

Preparation of (5R)-5-{4-[2-(5-ethylpyridin-2-yl)ethoxy]benzyl}-1,3-thiazolidine-2,4-dione (−)-O,O'-dibenzoyl-L-tartrate (3) using CH₃CN as solvent (ie a different solvent system from that used in the method of the invention)

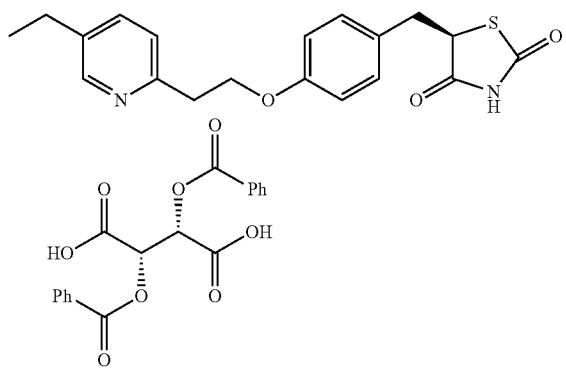

17a. A solution of L-DBTA (20.0 g, 55.86 mmol) in CH₃CN (15 mL) was added to a stirred slurry of 5-{4-[2-(5-ethylpyridin-2-yl)ethoxy]benzyl}-1,3-thiazolidine-2,4-dione (10.0 g, 28.08 mmol) in CH₃CN (15 mL). The reaction was heated at 70-72° C. for 1 h and filtered whilst hot. The filtered solid was washed with CH$_3$CN (30 mL) and dried to give the title compound (9.5 g). d.e. (method 7) 64.40%; Rt 7.79 min., 82.2%; Rt 11.48 min., 17.8%.

17b. A solution of L-DBTA (2.38 g) in CH$_3$CN (6 mL) was added to a slurry of the product from Example 17a (9.5 g) in CH$_3$CN (6 mL) at room temperature and stirred for 5 min. The reaction mixture was heated to 70° C. and CH$_3$CN (12 mL) added. Heating was continued at 70-72° C. for 1 h and the reaction filtered whilst hot. The solid was washed with CH$_3$CN (24 mL) and dried to give the title compound (7.5 g). d.e. (method 7) 79.70%; Rt 7.79 min., 89.80%; Rt 11.48 min., 10.20%.

17c. The procedure described in Example 17b was repeated twice to give the title compound (5.0 g). d.e. (method 7) 90.60%; Rt 7.79 min., 95.30%; Rt 11.48 min., 4.70%. Mp 154-158° C. IR (KBr) 3437, 3392, 3113, 3051, 2972, 2891, 2775, 1915, 1728, 1703, 1598, 1554, 1510, 1452, 1390, 1350, 1334, 1317, 1298, 1246 cm$^{-1}$. $^1$H NMR (400 MHz, DMSO-d$_6$) δ 14.25-13.60 (bs, 1 H, D$_2$O exchangeable), 12.05-12.00 (bs, 1 H, D$_2$O exchangeable), 8.37 (d, J=2.0 Hz, 1H), 8.02 (d, J=7.6 Hz, 4H), 7.73 (t, J=7.6 Hz, 2H), 7.60 (t, J=7.6 Hz, 5H), 7.29 (d, J=8.0 Hz, 1H), 7.13 (d, J=8.8 Hz, 2H), 6.86 (d, J=8.8 Hz, 2H), 5.88 (s, 2H), 4.86 (q, J=4.4 Hz, 1H), 4.30 (t, J=6.8 Hz, 2H), 3.30 (dd, J=4.0 & 10.0 Hz, 1H), 3.13 (t, J=6.8 Hz, 2H), 3.04 (dd, J=5.2 & 9.2 Hz, 1H), 2.60 (q, J=7.6 Hz, 2H), 1.17 (t, J=7.6 Hz, 3H). MS (Electrospray) 715 (M+1)$^+$, 379, 360, 357, 286, 241, 134. d.e. (Method 7) 95.40%. [α]$_D^{25}$+ 4.61° (c 1.0, DMSO).

Although material with high e.e. could be obtained from this process, the overall yield was low. This results in a very inefficient process.

Comparative Example 18

Preparation of (5R)-5-{4-[2-(5-ethylpyridin-2-yl)ethoxy]benzyl}-1,3-thiazolidine-2,4-dione(−)-O,O'-dibenzoyl-L-tartrate (3) using CH$_3$CN as solvent (ie a different solvent system from that used in the method of the invention)

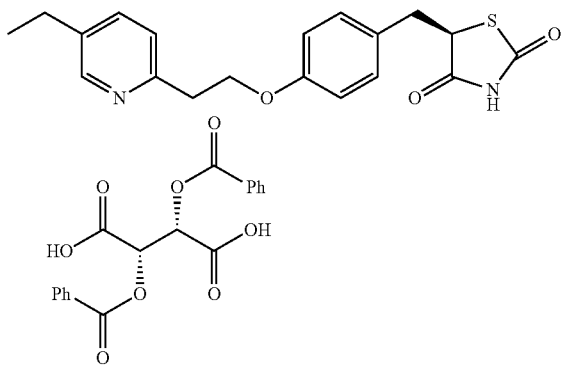

18a. 5-{4-[2-(5-Ethylpyridin-2-yl)ethoxy]benzyl}-1,3-thiazolidine-2,4-dione (25.0 g, 70.22 mmol) was added to a stirred solution of L-DBTA (50.0 g, 139.66 mmol) in CH$_3$CN (50 mL) at room temperature. The reaction was heated at 70-72° C. for 1 h, cooled to room temperature and filtered. The solid was washed with a minimum CH$_3$CN and dried to give the title compound (27.1 g). d.e. (method 7) 63.20%; Rt 7.79 min., 81.60%; Rt 11.48 min., 18.40%.

18b. The product from Example 18a (27.1 g) was added to a stirred solution of L-DBTA (6.8 g) in CH$_3$CN (170 mL) at room temperature. The reaction was heated to 70-72° C. for 1 h, cooled to room temperature and filtered. The solid was washed with minimum CH$_3$CN and dried to give the title compound (19.2 g). d.e. (method 7) 78.20%; Rt 7.79 min., 89.10%; Rt 11.48 min., 10.90%.

18c. The procedure described in Example 18b was repeated three times to give the title compound (13.2 g). d.e. (method 7) 89.4%; Rt 7.79 min., 94.70%; Rt 11.48 min., 5.30%. Characterisation data was identical to that obtained for Example 1, step 3.

Although material with high e.e. could be obtained from this process, the overall process was not reproducible on scale up.

The invention claimed is:

1. A dry powder pharmaceutical composition adapted for pulmonary administration by inhalation, the composition comprising:
   a glitazone, and
   one or more pharmaceutically acceptable carriers and/or excipients,
wherein the glitazone content of the composition consists of at least 95% by weight of the 5R enantiomer and less than 5% by weight of the 5S enantiomer, and
wherein the glitazone is pioglitazone or rosiglitazone or a pharmaceutically acceptable salt thereof.

2. The pharmaceutical composition according to claim 1, further comprising one or more therapeutic agents selected from the group consisting of steroids, β2-adrenoreceptor agonists, anticholinergic agents, bronchodilators, mucolytic agents, antitussive agents, leukotriene modulators, antibiotics, phosphodiesterase-IV inhibitors, non-steroidal anti-inflammatory agents, expectorant/mucokinetic modulators, p38MAP kinase inhibitors, and compounds which possess both β2-adrenoreceptor agonist and muscarinic antagonist activity in the same molecule.

3. The pharmaceutical composition according to claim 1, wherein the glitazone is pioglitazone or a pharmaceutically acceptable salt thereof.

4. The pharmaceutical composition according to claim 2, wherein the therapeutic agent is a corticosteroid.

5. The pharmaceutical composition according to claim 4, wherein the corticosteroid is selected from the group consisting of beclomethasone, flunisolide, fluticasone, ciclesonide, mometasone, mometasone desonide, rofleponide, hydrocortisone, prednisone, prednisolone, methyl prednisolone, naflocort, deflazacort, halopredone acetate, fluocinolone acetonide, fluocinonide, clocortolone, tipredane, prednicarbate, alclometasone dipropionate, halometasone, rimexolone, deprodone propionate, triamcinolone, betamethasone, fludrocortisone, desoxycorticosterone, etiprednol dicloacetate, GW-799943, GSK 870086, QAE397, NCX-1010, NCX-1020, NO-dexamethasone, PL-2146 and NS-126.

6. The pharmaceutical composition according to claim 2, wherein the therapeutic agent is a β2-adrenoreceptor agonist.

7. The pharmaceutical composition according to claim 6, wherein said β2-adrenoreceptor agonist is selected from the group consisting of albuterol, bambuterol, terbutaline, fenoterol, formoterol, formoterol fumarate, salmeterol, salmeterol xinafoate, arformoterol, arformoterol tartrate, indacaterol (QAB-149), carmoterol, picumeterol, olodaterol (BI 1744 CL), GSK159797, GSK59790, GSK159802, GSK642444, GSK678007, GSK961081, clenbuterol, procaterol, bitolterol and broxaterol.

8. The pharmaceutical composition according to claim 2, wherein the therapeutic agent is an anticholinergic agent.

9. The pharmaceutical composition according to claim 8, wherein the anticholinergic agent is a muscarinic antagonist.

10. The pharmaceutical composition according to claim 9, wherein the muscarinic antagonist is selected from the group consisting of ipratropium bromide, tiotropium, tiotropium bromide (Spiriva®), glycopyrollate (glycopyrronium bromide, NVA237), aclidinium (LAS34273), GSK656398, GSK233705, GSK 573719, LAS35201, QAT370 and oxytropium bromide.

11. The pharmaceutical composition according to claim 2, wherein the therapeutic agent possesses both β2-adrenoreceptor agonist and muscarinic antagonist activity in the same molecule.

12. The pharmaceutical composition according to claim 11, wherein the therapeutic agent possessing both β2-adrenoreceptor agonist and muscarinic antagonist activity in the same molecule is GSK961081.

13. The pharmaceutical composition according to claim 1, wherein the glitazone content of the composition consists of at least 97% by weight of the 5R enantiomer and less than 3% by weight of the 5S enantiomer.

14. The pharmaceutical composition according to claim 1, wherein the glitazone content of the composition consists of at least 98% by weight of the 5R enantiomer and less than 2% by weight of the 5S enantiomer.

15. The pharmaceutical composition according to claim 1, wherein the glitazone content of the composition consists of at least 99% by weight of the 5R enantiomer and less than 1% by weight of the 5S enantiomer.

16. The pharmaceutical composition according to claim 1, wherein the glitazone is in the form of microparticles having an average particle size (as equivalent d50) of less than 10 μm.

17. The pharmaceutical composition according to claim 16, wherein the glitazone is in the form of microparticles having an average particle size (as equivalent d50) of less than 5 μm.

* * * * *